United States Patent
Khan

(10) Patent No.: US 11,299,495 B2
(45) Date of Patent: Apr. 12, 2022

(54) SPIRO-LACTAM NMDA RECEPTOR MODULATORS AND USES THEREOF

(71) Applicant: Aptinyx Inc., Evanston, IL (US)

(72) Inventor: M. Amin Khan, Evanston, IL (US)

(73) Assignee: Aptinyx Inc., Evanston, IL (US)

( * ) Notice: Subject to any disclaimer, the term of this patent is extended or adjusted under 35 U.S.C. 154(b) by 0 days.

(21) Appl. No.: 16/321,905

(22) PCT Filed: Aug. 1, 2017

(86) PCT No.: PCT/US2017/044838
§ 371 (c)(1),
(2) Date: Jan. 30, 2019

(87) PCT Pub. No.: WO2018/026779
PCT Pub. Date: Feb. 8, 2018

(65) Prior Publication Data

US 2019/0177334 A1    Jun. 13, 2019

Related U.S. Application Data

(60) Provisional application No. 62/369,453, filed on Aug. 1, 2016.

(51) Int. Cl.
| | | |
|---|---|---|
| *C07D 487/10* | (2006.01) | |
| *C07D 471/10* | (2006.01) | |
| *A61P 25/28* | (2006.01) | |
| *A61P 25/02* | (2006.01) | |
| *A61P 25/22* | (2006.01) | |
| *A61P 25/18* | (2006.01) | |
| *A61P 25/14* | (2006.01) | |
| *A61P 25/24* | (2006.01) | |

(52) U.S. Cl.
CPC ............ *C07D 487/10* (2013.01); *A61P 25/02* (2018.01); *A61P 25/18* (2018.01); *A61P 25/22* (2018.01); *A61P 25/24* (2018.01); *A61P 25/28* (2018.01); *C07D 471/10* (2013.01)

(58) Field of Classification Search
CPC ..... C07D 487/10; C07D 471/10; A61P 25/28; A61P 25/02; A61P 25/22; A61P 25/18; A61P 25/14
See application file for complete search history.

(56) References Cited

U.S. PATENT DOCUMENTS

| | | |
|---|---|---|
| 4,904,681 A | 2/1990 | Cordi et al. |
| 4,959,493 A | 9/1990 | Ohfume et al. |
| 5,061,721 A | 10/1991 | Cordi et al. |
| 5,086,072 A | 2/1992 | Trullas et al. |
| 5,166,136 A | 11/1992 | Ward et al. |
| 5,168,103 A | 12/1992 | Kinney et al. |
| 5,350,769 A | 9/1994 | Kasai et al. |
| 5,523,323 A | 6/1996 | Maccecchini |
| 5,605,911 A | 2/1997 | Olney et al. |
| 5,648,259 A | 7/1997 | Mallet et al. |
| 5,741,778 A | 4/1998 | Martin et al. |
| 5,763,393 A | 6/1998 | Moskal et al. |
| 5,804,550 A | 9/1998 | Bourguignon |
| 5,902,815 A | 5/1999 | Olney et al. |
| 5,952,389 A | 9/1999 | Fogel |
| 5,959,075 A | 9/1999 | Lok et al. |
| 6,007,841 A | 12/1999 | Caruso |
| 6,025,471 A | 2/2000 | Deghenghi |
| 6,107,271 A | 8/2000 | Moskal et al. |
| 6,147,230 A | 11/2000 | Shimamoto et al. |
| 6,197,820 B1 | 3/2001 | Sontheimer et al. |
| 6,521,414 B2 | 2/2003 | Melcher et al. |
| 6,541,453 B2 | 4/2003 | Oldham et al. |
| 6,635,270 B2 | 10/2003 | Hong et al. |
| 6,667,317 B2 | 12/2003 | Chenard et al. |
| 6,821,985 B2 | 11/2004 | Chenard et al. |
| 6,828,318 B2 | 12/2004 | Snape et al. |
| 7,273,889 B2 | 9/2007 | Mermelstein et al. |
| 7,884,080 B2 | 2/2011 | Aslanian et al. |
| 8,097,634 B2 | 1/2012 | Ackermann et al. |
| 8,492,340 B2 | 7/2013 | Moskal |
| 9,504,670 B2 | 11/2016 | Lowe, III et al. |
| 9,512,133 B2 | 12/2016 | Khan et al. |
| 9,512,134 B2 | 12/2016 | Lowe, III et al. |
| 9,579,304 B2 | 2/2017 | Lowe, III et al. |
| 9,708,335 B2 | 7/2017 | Lowe, III et al. |
| 9,738,650 B2 | 8/2017 | Lowe, III et al. |
| 9,758,525 B2 | 9/2017 | Lowe, III et al. |

(Continued)

FOREIGN PATENT DOCUMENTS

| | | |
|---|---|---|
| CN | 1902202 A | 1/2007 |
| CN | 101066945 A | 11/2007 |

(Continued)

OTHER PUBLICATIONS

Kelleher et al., 66(19) Tetrahedron 3525-3536 (2010) (Year: 2010).*
Abbott AV et al., 'The Formalin Test: Scoring Properties of the First and Second Phases of the Pain Response in Rats,' Pain, Jan. 1995 (Jan. 1995), 60(1):91-102.
Abramets, II, 'Neurophysiological and Neurochemical Aspects of the Effects of Antidepressants and Mood Stabilizers,' Neurophysiol, Jan. 2008 (Jan. 2008), 40(1):64-78.
Alonso E et al., 'Spiro-Beta-Lactams as Beta-Turn Mimetics. Design, Synthesis, and NMR Conformational Analysis,' J Org Chem, Sep. 21, 2001 (Sep. 21, 2001), 66(19):6333-8.
Anonymous, Database Accession No. 1031928-30-9, Database Registry [Online] Chemical Abstracts Service, Columbus, Ohio, US; Jul. 1, 2008 (Jul. 1, 2008), XP002668992.

(Continued)

*Primary Examiner* — Timothy R Rozof
(74) *Attorney, Agent, or Firm* — Goodwin Procter LLP

(57) ABSTRACT

Disclosed are compounds having potency in the modulation of NMDA receptor activity. Such compounds can be used in the treatment of conditions such as depression and related disorders. Orally delivered formulations and other pharmaceutically acceptable delivery forms of the compounds, including intravenous formulations, are also disclosed.

18 Claims, No Drawings

(56) References Cited

U.S. PATENT DOCUMENTS

| | | |
|---|---|---|
| 9,802,946 B2 | 10/2017 | Khan et al. |
| 9,828,384 B2 | 11/2017 | Lowe, III et al. |
| 9,925,169 B2 | 3/2018 | Khan |
| 9,932,347 B2 | 4/2018 | Khan |
| 10,052,308 B2 | 8/2018 | Lowe, III et al. |
| 10,150,769 B2 | 12/2018 | Khan |
| 10,195,179 B2 | 2/2019 | Khan |
| 10,196,401 B2 | 2/2019 | Khan |
| 10,253,032 B2 | 4/2019 | Lowe, III et al. |
| 10,273,239 B2 | 4/2019 | Lowe, III et al. |
| 10,316,041 B2 | 6/2019 | Lowe, III et al. |
| 10,441,571 B2 | 10/2019 | Lowe, III et al. |
| 10,441,572 B2 | 10/2019 | Lowe, III et al. |
| 10,906,913 B2 | 2/2021 | Khan et al. |
| 10,918,637 B2 | 2/2021 | Khan |
| 10,961,189 B2 | 3/2021 | Khan |
| 11,028,095 B2 | 6/2021 | Khan |
| 2002/0103335 A1 | 8/2002 | Oldham et al. |
| 2003/0022253 A1 | 1/2003 | Moskal |
| 2003/0064921 A1 | 4/2003 | Millhauser et al. |
| 2003/0175734 A1 | 9/2003 | Kroes et al. |
| 2005/0037433 A1 | 2/2005 | Nakanishi et al. |
| 2005/0118286 A1 | 6/2005 | Suffin et al. |
| 2006/0063707 A1 | 3/2006 | Baudry et al. |
| 2006/0241046 A1 | 10/2006 | Olivera et al. |
| 2007/0087404 A1 | 4/2007 | Stahl et al. |
| 2007/0208001 A1 | 9/2007 | Zhuo et al. |
| 2009/0221544 A1 | 9/2009 | Stein et al. |
| 2010/0102616 A1 | 4/2010 | Yamasaki et al. |
| 2011/0159005 A1* | 6/2011 | Jacobson ............... A61K 31/35 424/158.1 |
| 2011/0306586 A1 | 12/2011 | Khan et al. |
| 2012/0295852 A1 | 11/2012 | Moskal |
| 2013/0005662 A1 | 1/2013 | Moskal |
| 2013/0035292 A1 | 2/2013 | Moskal et al. |
| 2013/0053325 A1 | 2/2013 | Moskal et al. |
| 2013/0150342 A1* | 6/2013 | Brain ................... C07D 498/20 514/210.21 |
| 2013/0310323 A1 | 11/2013 | Moskal |
| 2013/0316954 A1 | 11/2013 | Moskal |
| 2014/0107037 A1 | 4/2014 | Moskal |
| 2015/0051262 A1 | 2/2015 | Khan et al. |
| 2015/0105364 A1 | 4/2015 | Khan et al. |
| 2015/0336969 A1 | 11/2015 | Khan et al. |
| 2015/0368252 A1 | 12/2015 | Lowe, III et al. |
| 2015/0368253 A1 | 12/2015 | Lowe, III et al. |
| 2015/0368254 A1 | 12/2015 | Lowe, III et al. |
| 2015/0376195 A1 | 12/2015 | Lowe, III et al. |
| 2016/0122359 A1 | 5/2016 | Lowe, III et al. |
| 2016/0289240 A1 | 10/2016 | Lowe, III et al. |
| 2016/0368926 A1 | 12/2016 | Lowe, III et al. |
| 2017/0231956 A1 | 8/2017 | Lowe, III et al. |
| 2017/0333395 A1 | 11/2017 | Khan |
| 2017/0334922 A1 | 11/2017 | Khan |
| 2018/0092879 A1 | 4/2018 | Khan |
| 2018/0093994 A1 | 4/2018 | Khan |
| 2018/0127430 A1 | 5/2018 | Lowe, III et al. |
| 2018/0155354 A1 | 6/2018 | Lowe, III et al. |
| 2018/0179217 A1 | 6/2018 | Lowe, III et al. |
| 2018/0179218 A1 | 6/2018 | Lowe, III et al. |
| 2018/0215767 A1 | 8/2018 | Lowe, III et al. |
| 2018/0244680 A1 | 8/2018 | Lowe, III et al. |
| 2018/0250267 A1 | 9/2018 | Lowe, III et al. |
| 2018/0250268 A1 | 9/2018 | Lowe, III et al. |
| 2018/0291023 A1 | 10/2018 | Khan |
| 2019/0077807 A1 | 3/2019 | Khan et al. |
| 2019/0161442 A1 | 5/2019 | Khan |
| 2019/0175588 A1 | 6/2019 | Khan |
| 2019/0177334 A1 | 6/2019 | Khan |
| 2019/0194200 A1 | 6/2019 | Khan |
| 2019/0330209 A1 | 10/2019 | Khan |
| 2020/0181159 A1 | 6/2020 | Khan |
| 2020/0206189 A1 | 7/2020 | Lowe, III et al. |
| 2021/0002279 A1 | 1/2021 | Khan |
| 2021/0040095 A1 | 2/2021 | Khan |
| 2021/0047324 A1 | 2/2021 | Khan |
| 2021/0139489 A1 | 5/2021 | Madsen et al. |
| 2021/0155632 A1 | 5/2021 | Lowe, III et al. |

FOREIGN PATENT DOCUMENTS

| | | |
|---|---|---|
| CN | 101090902 A | 12/2007 |
| CN | 101125817 A | 2/2008 |
| CN | 102267995 A | 12/2011 |
| CN | 102918043 A | 2/2013 |
| CN | 103974712 A | 8/2014 |
| CN | 104321071 A | 1/2015 |
| CN | 105026401 A | 11/2015 |
| CN | 105229010 A | 1/2016 |
| CN | 105308049 A | 2/2016 |
| CN | 105408336 A | 3/2016 |
| EP | 0180398 A1 | 5/1986 |
| EP | 2542254 A1 | 1/2013 |
| EP | 2771021 | 5/2013 |
| JP | 2001261679 A | 9/2001 |
| JP | 2013519683 A | 5/2013 |
| JP | 2014520072 A | 8/2014 |
| RU | 2039035 C1 | 7/1995 |
| WO | WO-1996/032105 A1 | 10/1996 |
| WO | WO-1997/043306 A1 | 11/1997 |
| WO | WO-1999/024584 A1 | 5/1999 |
| WO | WO-1999/051985 A1 | 10/1999 |
| WO | WO-2000/027790 A1 | 5/2000 |
| WO | WO-2000/028090 A2 | 5/2000 |
| WO | WO-2001/36685 A2 | 5/2001 |
| WO | WO-2001/96606 A2 | 12/2001 |
| WO | WO-2001/98367 A2 | 12/2001 |
| WO | WO-2002/47535 A2 | 6/2002 |
| WO | WO-2002/072609 A2 | 9/2002 |
| WO | WO-2003/010540 A1 | 2/2003 |
| WO | WO-2004/005293 A2 | 1/2004 |
| WO | WO-2005/007656 A1 | 1/2005 |
| WO | WO-2005/020973 A2 | 3/2005 |
| WO | WO-2005/035535 A1 | 4/2005 |
| WO | WO-2005/047286 A1 | 5/2005 |
| WO | WO-2007/088041 A1 | 8/2007 |
| WO | WO-2007/103719 A2 | 9/2007 |
| WO | WO-2009/026319 A1 | 2/2009 |
| WO | WO-2009/039390 A2 | 3/2009 |
| WO | WO-2009/105718 A1 | 8/2009 |
| WO | WO-2009/156369 A1 | 12/2009 |
| WO | WO-2009/156396 A1 | 12/2009 |
| WO | WO-2010/015545 A1 | 2/2010 |
| WO | WO-2010/018213 A2 | 2/2010 |
| WO | WO-2010/033757 A1 | 3/2010 |
| WO | WO-2010/065709 A1 | 6/2010 |
| WO | WO-2010/102616 A1 | 9/2010 |
| WO | WO-2010/130665 A1 | 11/2010 |
| WO | WO-2011/003064 A2 | 1/2011 |
| WO | WO-2011/044089 A2 | 4/2011 |
| WO | WO-2011/100585 A1 | 8/2011 |
| WO | WO-2011/141728 A1 | 11/2011 |
| WO | WO-2012/021712 A1 | 2/2012 |
| WO | WO-2012/125598 A1 | 9/2012 |
| WO | WO-2012/149389 A2 | 11/2012 |
| WO | WO-2013/001448 A1 | 1/2013 |
| WO | WO-2013/014448 A1 | 1/2013 |
| WO | WO-2013/063120 A2 | 5/2013 |
| WO | WO-2014/011590 A2 | 1/2014 |
| WO | WO-2014/120783 A1 | 8/2014 |
| WO | WO-2014/120784 A1 | 8/2014 |
| WO | WO-2014/120789 A1 | 8/2014 |
| WO | WO-2014/120800 A1 | 8/2014 |
| WO | WO-2014120786 A1 | 8/2014 |
| WO | WO-2015/107495 A1 | 7/2015 |
| WO | WO-2016/042451 A1 | 3/2016 |
| WO | WO-2017/201283 A1 | 11/2017 |
| WO | WO-2017/201285 A1 | 11/2017 |
| WO | WO-2018/026763 A1 | 2/2018 |
| WO | WO-2018/026779 A1 | 2/2018 |
| WO | WO-2018/026782 A1 | 2/2018 |

(56) References Cited

FOREIGN PATENT DOCUMENTS

| | | |
|---|---|---|
| WO | WO-2018/026792 A1 | 2/2018 |
| WO | WO-2018/026798 A1 | 2/2018 |

OTHER PUBLICATIONS

Anonymous, Database Accession No. 1053605-89-2, Database Registry [Online] Chemical Abstracts Service, Columbus, Ohio, US; Sep. 28, 2008 (Sep. 28, 2008), XP002668993.

Anonymous, NCBI Submission NM_000149, 'Homo sapiens Fucosyltransferase 3 (galactoside 3(4)-L-fucosyltransferase, Lewis Blood Group)(FUT3), Transcript Variant 1, mRNA,' 1990 (1990), Retrieved from the internet; <<URL:http://www.ncbi.nlm.nih.gov/nuccore/148277008>>, pp. 1-5.

Anonymous, NCBI Submission NM_001276, 'Homo sapiens Chitinase 3-like 1 (cartilage glycoprotein-39)(CHI3L1), mRNA,' 1989 (1989), Retrieved from the internet; <URL:http://www.ncbi.nlm.nih.gov/nuccore/144226250>, pp. 1-5.

Anonymous, NCBI Submission NM_030979.1, 'Homo sapiens poly(A) Binding Protein, Cytoplasmic 3 (PABPC3), mRNA,' 2003 (2003), Retrieved from the internet; <URL:http://www.ncbi.nlm.nih.gov/nuccore/13569957>, pp. 1.

Anonymous, NCBI Submission NM_173216, 'Homo sapiens ST6 beta-galactosamide alpha-2,6-sialyltransferase 1 (ST6GAL1), transcript variant 1, mRNA,' 1989 (1989), Retrieved from the internet; <URL:http://www.ncbi.nlm.nih.gov/nuccore/27765090>, pp. 1-5.

Bennett GJ and Xie Y-K, 'A Peripheral Mononeuropathy in Rat That Produces Disorders of Pain Sensation Like Those Seen in Man,' Pain, Apr. 1988 (Apr. 1988), 33(1):87-107.

Bittermann H and Gmeiner P, 'Chirospecific Synthesis of Spirocyclic beta-Lactams and Their Characterization as Potent Type II beta-Turn Inducing Peptide Mimetics,' J Org Chem, Jan. 6, 2006 (Jan. 6, 2006), 71(1):97-102.

Bittermann H et al., 'A Highly Practical RCM Approach Towards a Molecular Building Kit of Spirocyclic Reverse Turn Mimics,' Chem Eur J, Aug. 16, 2006 (Aug. 16, 2006), 12(24):6315-22.

Burch RM et al., 'GLYX-13, an NMDA Receptor Glycine Site Functional Partial Agonist, Does Not Elicit Psychotomimetic Side Effects in Normal Human Volunteers at Doses Expected to be Therapeutic in Treatment-Resistant Major Depressive Disorder,' NCDEU, Jun. 16, 2010 (Jun. 16, 2010), Naurex, Inc., Evanston, IL (Publ), pp. 1 (Poster #unknown).

Burgdorf JS et al., 'Neurobiology of 50-kHz Ultrasonic Vocalizations in Rats: Electrode, Lesion, and Pharmacology Studies,' Behav Brain Res, Mar. 19, 2007 (Mar. 19, 2007) (ePub), 182(2):274-83.

Burgdorf JS et al., 'The Antidepressant and Anxiolytic Properties of GLYX-13: A Novel NMDA Receptor Glycine Site Functional Partial Agonist,' ACNP 2010 Meeting, Dec. 6, 2010 (Dec. 6, 2010), pp. 1 (Poster #198).

Burgdorf JS et al., 'The Effects of Selective Breeding for Differential Rates of 50-kHz Ultrasonic Vocalizations on Emotional Behavior in Rats,' Dev Psychobiol, Jan. 2009 (Jan. 2009), 51(1):34-46.

Burgdorf JS et al., 'The N-Methyl-D-Aspartate Receptor Modulator GLYX-13 Enhances Learning and Memory, in Young Adult and Learning Impaired Aging Rats,' Neurobiol Aging, May 14, 2009 (May 14, 2009) (ePub), 32(4):698-706.

Burgdorf JS et al., 'Uncovering the Molecular Basis of Positive Affect Using Rough-and-Tumble Play in Rats: A Role for the NMDA Receptor and Implications for Depression,' Neuroscience, Jul. 14, 2010, (Jul. 14, 2010) (ePub), 168(3):769-77.

Burgdorf JS et al., 'Uncovering the Molecular Basis of Positive Affect Using Rough-and-Tumble Play in Rats: A Role for the NMDA Receptor and Implications for Depression,' Neuroscience 38th Annual Meeting, Washington DC, Nov. 17, 2008 (Nov. 17, 2008), pp. 1-2 (Poster #393.1/UU11) [Electronically available Sep. 2008].

Careri M et al., 'Pentcopper(II) 12-Metallacrown-4 Complexes with alpha- and beta-Aminohydroxamic Acids in Aqueous Solution: A Reinvestigation,' J Inorg Chem, Jan. 15, 2003 (Jan. 15, 2003), 93(3-4):174-80.

Coates C et al., 'Product Class 9: Beta-Lactams,' Science of Synthesis, Georg Thieme Verlag KG, Stuttgart, DE (Pub), 2000 (2000), 21:609-46.

Cremonesi G et al., 'Enantiomerically Pure Polyheterocyclic Spiro-beta-Lactams from trans-4-Hydroxy-L-proline,' J Org Chem, Mar. 19, 2010 (Mar. 19, 2010), 75(6):2010-7.

Dalla Croce P and La Rosa C, 'Stereoselective Synthesis of N-Phenylsulfonyl Substituted Spiro-beta-Lactams,' Tetrahedron: Asymmetry, Mar. 26, 1999 (Mar. 26, 1999), 10(6):1193-9.

Dalla Croce P et al., 'Reaction of Mesoionic Compounds Deriving from Cyclic N-Acyl-alpha-amino Acids with N-(Phenylmethylene)benzenesulfonamide,' Tetrahedron, Jan. 1, 1999 (Jan. 1, 1999), 55(1):201-10.

Del Pozo C et al., 'Diastereo- and Enantioselective Synthesis of Novel beta-Lactam-Containing 1,4-Benzodiazepines Through a Ketene-Imine Cycloaddition Reaction,' Eur J Org Chem, Jan. 19, 2004 (Jan. 19, 2004), 2004(3):535-45.

Duman RS, 'Pathophysiology of Depression: The Concept of Synaptic Plasticity,' Eur Psychiatry, Jul. 2002 (Jul. 2002), 17(Suppl 3):306-10.

Erick M Carreira and Lisbet Kvaerno, Classics in Stereoselective Synthesis, (1st ed. 2009), Wiley-Vch Verlag GmbH & Co. KGaA, Weinham, DE (Publ), pp. 19-102 ISBN: 978-3-527-32452-1.

European Patent Office, Supplementary European Search Report (Form 1503) for EP 09 81 5233 (Fink D), completed at Munich DE dated Feb. 8, 2012 (dated Feb. 8, 2012) pp. 1-3.

European Patent Office, Supplementary European Search Report (Form 1503) for EP 10 82 2514 (Fink D), completed at Munich DE dated Feb. 1, 2013 (dated Feb. 1, 2013) pp. 1-2.

Export Data for 3 hydroxy 2 5 sulfonyl oxo2 5 diazaspiro, Apr. 22, 2016, Feb. 3, 2016, Jan. 30, 2016 and Mar. 26, 2015.

Forni A, 'Two Diastereoisomers of 2-(Benzenesulfonyl)-5-benzoyl-1-oxo-3-phenyl-2,5-diazaspiro[3.4]octan-7-yl acetate,' Acta Crystallographica Sec C: Crystal Structure Commun, Sep. 1998 (Sep. 1998), C54(9):1320-2.

Foster AC and Fagg GE, 'Neurobiology: Taking Apart NMDA Receptors,' Nature, Oct. 1, 1987 (Oct. 1, 1987), 329(6138):395-6.

Golik U, 'Synthesis of Malonimide Derivatives as Potential Penicillin Analogs,' J Heterocycl Chem, Feb. 1972 (Feb. 1972), 9(1):21-4.

Grigg R et al., 'X=Y-ZH Systems as Potential 1,3-Dipoles. Part 46. Cascade 1,3-Dipolar Cycloaddition Reactions of Cephalosporin Imines,' Tetrahedron, Nov. 1995 (Nov. 1995), 51(48):13347-56.

Haring R et al., 'Binding Studies and Photoaffinity Labeling Identify Two Classes of Phencyclidine Receptors in Rat Brain,' Biochemistry, Sep. 8, 1987 (Sep. 8, 1987), 26(18):5854-61.

Haring R et al., 'Glycine-Like Modulation of N-Methyl-D-Aspartate Receptors by a Monoclonal Antibody that Enhances Long-Term Potentiation,' J Neurochem, Jul. 1991 (Jul. 1991), 57(1):323-32.

Haring R et al., 'Identification of Polypeptides of the Phencyclidine Receptor of Rat Hippocampus by Photoaffinity Labeling with [H3]Azidophencyclidine,' Biochemistry, Feb. 11, 1986 (Feb. 11, 1986), 25(3):612-20.

Haring R et al., 'Multiple Mode of Binding of Phencyclidines: High Affinity Association Between Phencyclidine Receptors in Rat Brain and a Monovalent Ion-Sensitive Polypeptide,' Biochem Biophys Res Commun, Jan. 30, 1987 (Jan. 30, 1987), 142(2):501-10.

Holderbach R et al., 'Enhanced Long-Term Synaptic Depression in an Animal Model of Depression,' Biol Psychiatry, Dec. 4, 2006 (Dec. 4, 2006) (ePub), 62(1):92-100.

International Search Report and Written Opinion for International Application No. PCT/US2017/033323, dated Jul. 17, 2017, 12 pages.

International Search Report and Written Opinion for International Application No. PCT/US2017/033326, dated Jul. 10, 2017, 12 pages.

(56) References Cited

OTHER PUBLICATIONS

International Search Report and Written Opinion for International Application No. PCT/US2017/044813, dated Oct. 19, 2017, 13 pages.
International Search Report and Written Opinion for International Application No. PCT/US2017/044838, dated Oct. 19, 2017, 11 pages.
International Search Report and Written Opinion for International Application No. PCT/US2017/044841, dated Oct. 23, 2017, 11 pages.
International Search Report and Written Opinion for International Application No. PCT/US2017/044861, dated Oct. 19, 2017, 11 pages.
International Search Report and Written Opinion for International Application No. PCT/US2017/044871, dated Oct. 19, 2017, 13 pages.
International Searching Authority, International Search Report (ISA/210) for Application No. PCT/US08/77045, (Young LW), completed on Mar. 28, 2009 (Mar. 28, 2009) and dated Apr. 29, 2009 (dated Apr. 29, 2009), pp. 1-3.
International Searching Authority, International Search Report (ISA/210) for Application No. PCT/US09/57401, (Young LW), completed Dec. 6, 2009 (Dec. 6, 2009) and dated Dec. 24, 2009 (dated Dec. 24, 2009), pp. 1-2.
International Searching Authority, International Search Report (ISA/210) for Application No. PCT/US09/66536, (Kang YJ), completed Aug. 9, 2010 (Aug. 9, 2010) and dated Aug. 9, 2010 (dated Aug. 9, 2010), pp. 1-5.
International Searching Authority, International Search Report (ISA/210) for Application No. PCT/US2014/013619, (Wolf C), completed Mar. 6, 2014 (Mar. 6, 2014) and dated Mar. 20, 2014 (dated Mar. 20, 2014), pp. 1-3.
International Searching Authority, International Search Report (ISA/210) for Application No. PCT/US2014/013621, (Wolf C), completed Feb. 27, 2014 (Feb. 27, 2014) and dated Mar. 13, 2014 (dated Mar. 13, 2014), pp. 1-2.
International Searching Authority, International Search Report (ISA/210) for Application No. PCT/US2014/013623, (Wolf C), completed Mar. 3, 2014 (Mar. 3, 2014) and dated Mar. 13, 2014 (dated Mar. 13, 2014), pp. 1-3.
International Searching Authority, International Search Report (ISA/210) for Application No. PCT/US2014/013626, (Rudolf M), completed Mar. 10, 2014 (Mar. 10, 2014) and dated Mar. 18, 2014 (dated Mar. 18, 2014), pp. 1-4.
International Searching Authority, International Search Report (ISA/210) for Application No. PCT/US2014/013639, (Wolf C), completed Feb. 28, 2014 (Feb. 28, 2014) and dated Mar. 13, 2014 (dated Mar. 13, 2014), pp. 1-3.
International Searching Authority, Written Opinion of Application No. PCT/US2008/077045 (ISA/237), (Young LW), completed Mar. 28, 2009 (Mar. 28, 2009) and dated Mar. 24, 2010 (dated Mar. 24, 2010), pp. 1-8.
International Searching Authority, Written Opinion of Application No. PCT/US2009/057401 (ISA/237), (Young LW), completed Dec. 6, 2009 (Dec. 6, 2009) and dated Mar. 22, 2011 (dated Mar. 22, 2011), pp. 1-6.
International Searching Authority, Written Opinion of Application No. PCT/US2009/066536 (ISA/237), (Kang YJ), completed Aug. 9, 2010 (Aug. 9, 2010) and dated Jun. 7, 2011 (dated Jun. 7, 2011), pp. 1-8.
International Searching Authority, Written Opinion of Application No. PCT/US2014/013619 (ISA/237), (Wolf C), completed Mar. 6, 2014 (Mar. 6, 2014) and dated Aug. 4, 2015 (dated Aug. 4, 2015), pp. 1-4.
International Searching Authority, Written Opinion of Application No. PCT/US2014/013621 (ISA/237), (Wolf C), completed Feb. 27, 2014 (Feb. 27, 2014) and dated Aug. 4, 2015 (dated Aug. 4, 2015), pp. 1-6.
International Searching Authority, Written Opinion of Application No. PCT/US2014/013623 (ISA/237), (Wolf C), completed Mar. 3, 2014 (Mar. 6, 2014) and dated Aug. 4, 2015 (dated Aug. 4, 2015), pp. 1-4.
International Searching Authority, Written Opinion of Application No. PCT/US2014/013626 (ISA/237), (Rudolf M, completed Mar. 10, 2014 (Mar. 10, 2014) and dated Aug. 4, 2015 (dated Aug. 4, 2015), pp. 1-6.
International Searching Authority, Written Opinion of Application No. PCT/US2014/013639 (ISA/237), (Wolf C), completed Feb. 28, 2014 (Feb. 28, 2014) and dated Aug. 4, 2015 (dated Aug. 4, 2015), pp. 1-4.
Johnson JA et al., 'The Preparation of a Double Metallahelicate Containing 28 Copper Atoms,' Angew Chem Int Ed Engl, Feb. 3, 2003 (Feb. 3, 2003), 42(5):546-9.
Johnson KM and Jones SM, 'Neuropharmacolgy of Phencyclidine: Basic Mechanisms and Therapeutic Potential,' Annu Rev Pharmacol Toxicol, 1990 (1990), 30:707-50.
Khasanov AB et al., 'Novel Asymmetric Approach to Proline-Derived Spiro-beta-Lactams,' J Org Chem., Aug. 20, 2004 (Aug. 20, 2004), 69(17):5766-9.
Kloog Y et al., 'Kinetic Characterization of the Phencyclidine-N-Methyl-d-asparate Receptor Interaction: Evidence for a Steric Blockade of the Channel,' Biochemistry, Feb. 9, 1988 (Feb. 9, 1988), 27(3):843-8.
Kloog Y et al., 'Mode of Binding of [3H]dibenzocycloalkenimine (MK-801) to the N-methyl-D-Aspartate (NMDA) Receptor and its Therapeutic Implication,' FEBS Letts, Mar. 28, 1988 (Mar. 28, 1988), 230(1-2):167-70.
Koller M and Urwyler S, 'Novel N-Methyl-D-aspartate Receptor Antagonists: A Review of Compounds Patented Since 2006,' Expert Opin Ther Pat, Nov. 8, 2010 (Nov. 8, 2010) (epub), 20(12):1683-702.
Kroes RA et al., 'Development of a Novel Glycobiologic Therapy for Glioblastoma,' Neuro-oncol, Oct. 2006 (Oct. 2006), 8(4):397-8, (Abstract #CB-14).
Kroes RA et al., 'Development of a Novel Glycobiology-Based Therapeutic for Glioblastoma,' J Neurochem, Nov. 10, 2006 (Nov. 10, 2006), 99(Suppl. 1):17 (Abstract #50).
Krystall JH et al., 'NMDA Agonists and Antagonists as Probes of Glutamatergic Dysfunction and Pharmacotherapies in Neuropsychiatric Disorders,' Harvard Rev Psychiatry, Sep.-Oct. 1999 (Sep.-Oct. 1999), 7(3):125-43.
Leander JD et al., 'Lack of Ketamine-Like Discriminative Effects of GLYX-13: A Novel NMDA Receptor Glycine Site Functional Partial Agonist with Antidepressant-Like Preclinical Effects,' ACNP 49th Annual Meeting, Dec. 2010 (Dec. 2010), Miami Beach, FL, Naurex, Inc., Evanston, IL (Pub) (Poster #218).
Li G-Q et al., 'N-Heterocyclic Carbene Catalyzed Ring Expansion of 4-Formyl-beta-lactams: Synthesis of Succinimide Derivatives,' Org Lett, Aug. 9, 2007 (Aug. 9, 2007) (ePub), 9(18):3519-21.
Lynch G et al., 'Synaptic Pasticity in Early Aging,' Ageing Res Rev, Aug. 28, 2006 (Aug. 28, 2006) (ePub), 5(3):255-80.
Macias A et al., 'Diastereoselective [2+2]-Cycloaddition Reactions of Unsymmetrical Cyclic Ketenes with Imines: Synthesis of Modified Prolines and Theoretical Study of the Reaction Mechanism,' J Org Chem, Oct. 1, 2004 (Oct. 1, 2004) Sep. 10, 2005 (Sep. 10, 2005)(ePub), 69(21):7004-12.
Macias A et al., 'Unusual Rearrangement of Spiro-beta-Lactams to 1,4-diazabicyclo[4,4,0]decanes and 1,4-diazabicyclo[4,3,0]nonanes. Synthesis of Conformationally Restricted Sigma-Receptor Ligands,' Tetrahedron Lett, Jun. 2004 (Jun. 2004), 45(24):4657-60.
Marcias A et al., 'Synthesis of Enantiopure Pyrrolidine-Derived Peptidomimetics and Oligo-beta-Peptides via Nucleophilic Ring-Opening of beta-Lactams,' J Org Chem, Sep. 29, 2006 (Sep. 29, 2006), 71(20):7721-30.
Mayer ML and Miller RJ, 'Excitatory Amino Acid Receptors, Second Messengers and Regulation of Intracellular Ca2+ in Mammalian Neurons,' Trends Pharmacol Sci, Jun. 1990 (Jun. 1990), 11(6):254-60.
McLeod MN et al., 'Chromium Potentiation of Antidepressant Pharmacotherapy for Dysthymic Disorder in 5 Patients,' J Clin Psychiatry, Apr. 1999 (Apr. 1999), 60(4):237-40.

(56) References Cited

OTHER PUBLICATIONS

Mishra H et al., 'Three-Dimensional Quantitative Structure-Activity Relationship and Comparative Molecular Field Analysis of Dipeptide Hydroxamic Acid Helicobacter pylori Urease Inhibitors,' Antimicrob Agents Chemother, Aug. 2002 (Aug. 2002), 46(8):2613-8.
Monahan JB et al., 'D-Cycloserine, a Positive Modulator of the N-Methyl-d-Asparate Receptor, Enhances Performance of Learning in Rats,' Pharmacol Biochem Behav, Nov. 1989 (Nov. 1989), 34(3):649-53.
Moskal JR and Burgdorf JS, 'The Antidepressant and Anxiolytic Properties of GLYX-13: A Novel NMDA Receptor Glycine Site Functional Partial Agonist,' ACNP 29th Annual Meeting, Dec. 7, 2009 (Dec. 7, 2009), Hollywood, FL, Naurex, Inc. Evanston, IL (Pub) (Poster #059).
Moskal JR and Schaffner AE, 'Monoclonal Antibodies to the Dentate Gyrus: Immunocytochemical Characterization and Flow Cytometric Analysis of Hippocampal Neurons Bearing a Unique Cell-Surface Antigen,' J Neurosci, Jul. 1986 (Jul. 1986), 6(7):2045-53.
Moskal JR et al., 'A Novel Approach to Unlocking the Therapeutic Potential of the NMDA Receptor,' Vital Signs e-Magazine, Sep. 2010 (Sep. 2010), pp. 1-2.
Moskal JR et al., 'GLYX-13: A Monoclonal Antibody-Derived Peptide that Acts as an N-Methyl-D-Aspartate Receptor Modulator,' Neuropharmacol, Jul. 26, 2005 (Jul. 26, 2005) (ePub), 49(7):1077-87.
Moskal JR et al., 'The Use of Antibody Engineering to Create Novel Drugs that Target N-Methyl-D-Aspartate Receptors,' Curr Drug Targets, Sep. 2001 (Sep. 2001), 2(3):331-45.
Moskal JR, 'The Anti-depressant and Anxiolytic Properties of GLYX-13: A Glycine-site Functional Partial Agonist (GFPA), a Novel Mechanism for Modulating NMDA,' ACNP 48th Annual Meeting, Dec. 7, 2009 (Dec. 7, 2009), Hollywood, FL, pp. 1-2 (Abstract).
Myers SM and Johnson CP, 'Management of Children with Autism Spectrum Disorders,' Pediatrics, Oct. 29, 2007 (Oct. 29, 2007) (ePub), 120(5):1162-82.
Narahashi T et al., 'Mechanisms of Action of Cognitive Enhancers on Neuroreceptors,' Biol Pharm Bull, Nov. 2004 (Nov. 2004), 27(11):1701-6.
Overman LE and Osawa T, 'A Convenient Synthesis of 4-Unsubstituted beta-Lactams,' J Am Chem Soc, Mar. 1985 (Mar. 1985), 107(6):1698-701.
Parac-Vogt TN et al., 'Pentacopper(II) Complexes of alpha-Aminohydroxamic Acids: Uranyl-Induced Conversion of a 12-Metallacrown-4 to a 15-Metallacrown-5,' J Inorg Biochem, Nov. 21, 2004 (Nov. 21, 2004) (ePub), 99(2):497-504.
Patani et al., "Bioisosterism: A Rational Approach in Drug Design," Chem. Rev., Jan. 1, 1997, 96(8):3147-3176.
Pittenger C et al., 'The NMDA Receptor as a Therapeutic Target in Major Depressive Disorder,' CNS Neurol Disord Targets, Apr. 2007 (Apr. 2007), 6(2):101-15.
Raghavan B et al., 'Allosteric Modulation of the Dopamine D2 Receptor by Pro-Leu-Gly-NH2 Peptidomimetics Constrained in Either a Polyproline II Helix or a Type II beta-Turn Conformation,' J Med Chem, Apr. 9, 2009 (Apr. 9, 2009), 52(7):2043-51.
Ransom RW and Stec NL, 'Cooperative Modulation of [3H]MK-801 Binding to the N-Methyl-d-Asparate Receptor-Ion Channel Complex by I-Glumate, Glycine, and Polyamines,' J Neurochem, Sep. 1988 (Sep. 1988), 51(3):830-6.
Rasmusson GH et al., '6-Substituted Penicillin Derivatives,' Tetrahedron Lett, 1973 (1973), 14(2):145-8.
Rautio J et al., 'Prodrugs: Design and Clinical Applications,' Nat Rev Drug Discov, Mar. 2008 (Mar. 2008), 7(3):255-70.
Schell MJ, 'The N-methyl D-aspartate Receptor Glycine Site and D-serine Metabolism: An Evolutionary Perspective,' Philos Trans R Soc Lond B Biol Sci, Jun. 29, 2004 (Jun. 29, 2004), 359(1446):943-64.
Shankar GM and Walsh DM, 'Alzheimer's Disease: Synaptic Dysfunction and A-beta,' Mol Neurodegener, Nov. 23, 2009 (Nov. 23, 2009), 4:48-61.
Siemion IZ et al., 'Conformational Preferences of the Sequential Fragments of the Hinge Region of the Human IgA1 Immunoglobulin Molecule,' Biophys Chem, Aug. 1988 (Aug. 1988), 31(1-2):35-44.
Simplicio AL et a;., 'Prodrugs for Amines,' Molecules, Mar. 2008 (Mar. 2008), 13(3):519-47.
Singapore Search Report and Written Opinion Issued for corresponding Singapore application No. 11201505860X, dated Apr. 18, 2016.
Singapore Search Report and Written Opinion Issued for corresponding Singapore application No. 11201505862T, dated Apr. 18, 2016.
Singapore Search Report and Written Opinion Issued for corresponding Singapore application No. 11201505934X, dated Apr. 27, 2016.
Singapore Search Report and Written Opinion Issued for corresponding Singapore application No. 11201505937S, dated May 5, 2016.
Singapore Search Report and Written Opinion Issued for corresponding Singapore application No. 11201505942Y, dated Mar. 22, 2016.
Stanton PK et al., 'Inhibition of the Production and Maintenance of Long-Term Potentiation in Rat Hippocampal Slices by a Monoclonal Antibody,' Proc Natl Acad Sci USA, Mar. 1987 (Mar. 1987), 84(6):1684-8.
Stanton PK et al., 'Neuroprotection by a Novel NMDAR Functional Glycine Site Partial Agonist, GLYX-13,' Neuroreport, Aug. 26, 2009 (Aug. 26, 2009), 20(13):1193-7.
Tanwar MK et al., 'Gene Expression Microarray Analysis Reveals YLK-40 to be a Potential Serum Marker for Malignant Character in Human Glioma,' Cancer Res, Aug. 1, 2002 (Aug. 1, 2002), 62(15):4364-8.
Thompson LT et al., 'Hippocampus-Dependent Learning Facilitated by a Monoclonal Antibody or D-Cycloserine,' Nature, Oct. 15, 1992 (Oct. 15, 1992), 359(6396):638-41.
Turturro A et al., 'Growth Curves and Survival Characteristics of the Animals Used in the Biomarkers of Aging Program,' J Gerentol A Biol Sci Med Sci, Nov. 1999 (Nov. 1999), 54A(11):B492-B501.
Various, *The NMDA Receptor*, (2nd ed. 1994), GL Collingridge and JC Watkins Eds., Oxford University Press, Inc., New York, New York US (Publ), pp. 1-479 ISBN: 0-19-262371-0.
Wood PL et al., 'Antinociceptive Action of GLYX-13: An N-Methyl-D-aspartate Receptor Glycine Site Partial Agonist,' Neuroreport, Jul. 2, 2008 (Jul. 2, 2008), 19(10):1061-3.
Wood PL, 'The NMDA Receptor Complex: A Long and Winding Road to Therapeutics,' IDrugs, Mar. 2005 (Mar. 2005), 8(3):229-35.
Wood SG et al., 'Tetrapeptide Inhibitors of the IgA1 Proteinases from Type I Neisseria gonorrhoeae,' J Med Chem, Oct. 1989 (Oct. 1989), 32(10):2407-11.
Zhang X-L et al., 'A NMDA Receptor Glycine Site Partial Agonist, GLYX-13, Simultaneously Enhances LTP and Reduces LTD at Schaffer Collateral-CA1 Synapses in Hippocampus,' Neuropharmacology, Aug. 29, 2008 (Aug. 29, 2008), 55(7):1238-50.
U.S. Appl. No. 13/051,237, filed Mar. 18, 2011, NMDA Receptor Modulators and Uses Thereof, Abandoned, US 2011-0306586 Published on Dec. 15, 2011.
U.S. Appl. No. 14/050,641, filed Oct. 10, 2013, NMDA Receptor Modulators and Uses Thereof, Patented, U.S. Pat. No. 9,512,133 Issued Dec. 6, 2016.
U.S. Appl. No. 14/580,803, filed Dec. 23, 2014, NMDA Receptor Modulators and Uses Thereof, Patented, U.S. Pat. No. 9,802,946 Issued Oct. 31, 2017.
U.S. Appl. No. 15/785,603, filed Oct. 17, 2017, NMDA Receptor Modulators and Uses Thereof, Published, US 2019-0077807 Published on Mar. 14, 2019.
U.S. Appl. No. 16/006,125, filed Jun. 12, 2018, Spiro-Lactam NMDA Modulators and Methods of Using Same, Patented, U.S. Pat. No. 10,150,769 Issued on Dec. 11, 2018.
U.S. Appl. No. 16/197,584, filed Nov. 21, 2018, Spiro-Lactam NMDA Modulators and Methods of Using Same, Pending.

(56) References Cited

OTHER PUBLICATIONS

U.S. Appl. No. 16/322,604, filed Feb. 1, 2019, Spiro-Lactam NMDA Modulators and Methods of Using Same, Pending, US 2019-0194200 Published on Jun. 27, 2019.
U.S. Appl. No. 14/764,395, filed Jul. 29, 2015, Spiro-Lactam NMDA Receptor Modulators and Uses Thereof, Patented, U.S. Pat. No. 9,512,134 Issued Dec. 6, 2016.
U.S. Appl. No. 14/932,579, filed Nov. 4, 2015, Spiro-Lactam NMDA Receptor Modulators and Uses Thereof, Patented, U.S. Pat. No. 9,504,670 Issued Nov. 29, 2016.
U.S. Appl. No. 15/049,577, filed Feb. 22, 2016, Spiro-Lactam NMDA Receptor Modulators and Uses Thereof, Patented, U.S. Pat. No. 9,579,304 Issued Feb. 28, 2017.
U.S. Appl. No. 15/337,605, filed Oct. 28, 2016, Spiro-Lactam NMDA Receptor Modulators and Uses Thereof, Patented, U.S. Pat. No. 10,052,308 Issued on Aug. 21, 2018.
U.S. Appl. No. 15/969,186, filed May 2, 2018, Spiro-Lactam NMDA Receptor Modulators and Uses Thereof, Published, US 2018-0250267 Published on Sep. 6, 2018.
U.S. Appl. No. 15/969,200, filed May 2, 2018, Spiro-Lactam NMDA Receptor Modulators and Uses Thereof, Published, US 2018-0250268 Published on Sep. 6, 2018.
U.S. Appl. No. 14/764,402, filed Jul. 29, 2015, Spiro-Lactam NMDA Receptor Modulators and Uses Thereof, Patented, U.S. Pat. No. 9,828,384 Issued Nov. 28, 2017.
U.S. Appl. No. 15/671,409, filed Aug. 8, 2017, Spiro-Lactam NMDA Receptor Modulators and Uses Thereof, Published, US 2018-0179218 Published on Jun. 28, 2018.
U.S. Appl. No. 15/938,040, filed Mar. 28, 2018, Spiro-Lactam NMDA Receptor Modulators and Uses Thereof, Published, US 2018-0215767 Published on Aug. 2, 2018.
U.S. Appl. No. 15/968,976, filed May 2, 2018, Spiro-Lactam NMDA Receptor Modulators and Uses Thereof, Published, US 2018-0244680 Published on Aug. 30, 2018.
U.S. Appl. No. 14/764,411, filed Jul. 29, 2015, Spiro-Lactam NMDA Receptor Modulators and Uses Thereof, Published, U.S. Pat. No. 9,758,525 Issued Sep. 12, 2017.
U.S. Appl. No. 15/667,014, filed Aug. 2, 2017, Spiro-Lactam NMDA Receptor Modulators and Uses Thereof, Published, US 2018-0179217 Published on Jun. 28, 2018.
U.S. Appl. No. 14/764,419, filed Jul. 29, 2015, Spiro-Lactam NMDA Receptor Modulators and Uses Thereof, Patented, U.S. Pat. No. 9,738,650 Issued Aug. 22, 2017.
U.S. Appl. No. 15/653,738, filed Jul. 19, 2017, Spiro-Lactam NMDA Receptor Modulators and Uses Thereof, Patented, U.S. Pat. No. 10,253,032 Issued Apr. 9, 2019.
U.S. Appl. No. 14/764,426, filed Jul. 29, 2015, Spiro-Lactam NMDA Receptor Modulators and Uses Thereof, Patented, U.S. Pat. No. 9,708,335 Issued Jul. 18, 2017.
U.S. Appl. No. 15/625,163, filed Jun. 16, 2017, Spiro-Lactam NMDA Receptor Modulators and Uses Thereof, Published, US 2018-0127430 Published on May 10, 2018.
U.S. Appl. No. 16/321,901, filed Jan. 30, 2019, Spiro-Lactam NMDA Receptor Modulators and Uses Thereof, Pending, US 2019-0161442 Published on May 30, 2019.
U.S. Appl. No. 16/321,903, filed Jan. 30, 2019, Spiro-Lactam NMDA Receptor Modulators and Uses Thereof, Pending, US 2019-0175588 Published on Jun. 13, 2019.
U.S. Appl. No. 16/321,906, filed Jan. 30, 2019, Spiro-Lactam and Bis-Spiro-Lactum NMDA Receptor Modulators and Uses Thereof, Pending.
U.S. Appl. No. 15/638,669, filed Jun. 30, 2017, Spiro-Lactam NMDA Receptor Modulators and Uses Thereof, Patentd, U.S. Pat. No. 9,932,347 Issued Apr. 3, 2018.
U.S. Appl. No. 15/830,378, filed Dec. 4, 2017, Spiro-Lactam NMDA Receptor Modulators and Uses Thereof, Patented, U.S. Pat. No. 10,196,401 Issued on Feb. 5, 2019.
U.S. Appl. No. 15/636,888, filed Jun. 29, 2017, Spiro-Lactam NMDA Receptor Modulators and Uses Thereof, Patented, U.S. Pat. No. 9,925,169 Issued Mar. 27, 2018.
U.S. Appl. No. 15/830,383, filed Dec. 4, 2017, Spiro-Lactam NMDA Receptor Modulators and Uses Thereof, Patented, U.S. Pat. No. 10,195,179 Issued on Feb. 5, 2019.
Anonymous, Database Accession No. 1203799-75-0, Database Registry [Online] Chemical Abstracts Service, Columbus, Ohio, US; Jan. 28, 2010.
Anonymous, Database Accession No. 1221818-08-1, Database Registry [Online] Chemical Abstracts Service, Columbus, Ohio, US; May 7, 2010.
Anonymous, Database Accession No. 383429-00-3, Database Registry [Online] Chemical Abstracts Service, Columbus, Ohio, US; Jan. 16, 2002.
Aptinyx Press Release, "Aptinyx Announces Results of Phase 2 Fibromyalgia Study of NYX-2925 Have Been Selected for Late-Breaking Presentation at the American College of Rheumatology Annual Meeting," dated Oct. 28, 2019, 2 pages.
Aptinyx Press Release, "Aptinyx Exploratory Clinical Studies Provide First Evidence that NYX-2925 Elicits Rapid, Persistent, NMDAr-Mediated Pharmacodynamic Activity in Humans," dated Nov. 12, 2018, 2 pages.
Aptinyx Press Release, "Aptinyx Initiates Two Phase 2 Studies of NYX-2925 in Patients with Chronic Centralized Pain Conditions," dated Nov. 12, 2019, 2 pages.
Aptinyx Press Release, "Aptinyx Reports Positive Data from Interim Analysis of Exploratory Study of NYX-2925 in Subjects with Fibromyalgia," dated Dec. 3, 2018, 2 pages.
Aptinyx Press Release, "Aptinyx Reports Top-line Results from Phase 2 Clinical Study of NYX-2925 in Painful Diabetic Peripheral Neuropathy," dated Jan. 16, 2019, 2 pages.
Aptinyx Press Release, "Robust Analgesic Activity of Aptinyx's NYX-2925 in Advanced DPN Patients Revealed Through Further Analysis of Data from Phase 2 Study," dated Apr. 18, 2019, 2 pages.
Fantò et al., "Design, Synthesis, and In Vitro Activity of Peptidomimetic Inhibitors of Myeloid Differentiation Factor 88," J. Med. Chem. 51(5):1189-1202 (2008).
FDA mulls drug to slow late-stage Alzheimer's [online] retrieved from the internet; Sep. 24, 2003; URL: http://www.cnn.com/ 2003/ HEALTH/conditions/09/24/alzheimers.drug.ap/index.html.
Golub et al., "Molecular Classification of Cancer: Class Discovery and Class Prediction by Gene Expression Monitoring," Science, 286:531-536, Oct. 15, 1999.
Ikeda et al. Document No. 101:54757, retrieved from STN; entered in STN on Aug. 18, 1984.
Kelleher et al., "Structure-reactivity relationships of L-proline derived spirolactams and -methyl prolinamide organocatalysts in the asymmetric Michael addition reaction of aldehydes to nitroolefins," Tetrahedron, 66(19): 3525-3536 (2010).
Krafft et al., "A straightforward and efficiently scaleable synthesis of novel racemic 4-substituted-2,8-diazaspiro[4,5]decan-1-one derivatives," Synthesis, 19:3245-3252 (2005).
Lala et al., "Role of nitric oxide in tumor progression: Lessons from experimental tumors," Cancer and Metastasis Reviews, 17:91-106, 1998.
Liu et al. Document No. 120:244445, retrieved from STN; entered in STN on May 14, 1994.
McMaster et al. Document No. 157:133191, retrieved from STN; entered in STN on Jun. 3, 2012.
Nagamori et al. Document No. 163:374386, retrieved from STN; entered in STN on Aug. 27, 2015.
Newcomer et al. "NMDA receptor function, memory, and brain aging," Dialogues in Clinical Neuroscience, 2(3):219-232 (2000).
Rajaganapathy et al., "Small Molecular Inhibitor Design for NCoR-SIN3A-HDAC Complex in Acute Myeloid Leukemia by Computational Approach," Journal of Pharmacy Research, 5(11):5127-5130 (2012).
CAS Registry No. 1026351-34-7, STN Entry Date Jun. 8, 2008.
CAS Registry No. 1071615-85-4, STN Entry Date Nov. 7, 2008.
CAS Registry No. 1071753-92-8, STN Entry Date Nov. 9, 2008.
CAS Registry No. 1279880-57-7, STN Entry Date Apr. 14, 2011.
CAS Registry No. 1334412-71-3, STN Entry Date Oct. 5, 2011.
CAS Registry No. 1334414-40-2, STN Entry Date Oct. 5, 2011.
CAS Registry No. 1402667-30-4, STN Entry Date Nov. 1, 2012.
CAS Registry No. 1545253-26-6, STN Entry Date Feb. 16, 2014.

(56) References Cited

OTHER PUBLICATIONS

CAS Registry No. 1782369-96-3, STN Entry Date Jun. 17, 2015.
CAS Registry No. 1783759-59-0, STN Entry Date Jun. 18, 2015.
CAS Registry No. 1785248-52-3, STN Entry Date Jun. 21, 2015.
CAS Registry No. 194598-54-4, STN Entry Date Sep. 26, 1997.
CAS Registry No. 646055-59-6, STN Entry Date Feb. 4, 2004.
CAS Registry No. 765262-11 -1, STN Entry Date Oct. 19, 2004.
CAS Registry No. 769912-53-0, STN Entry Date Oct. 26, 2004.
CAS Registry No. 771467-12-0, STN Entry Date Oct. 28, 2004.
CAS Registry No. 773840-22-5, STN Entry Date Nov. 2, 2004.
CAS Registry No. 775570-69-9, STN Entry Date Nov. 7, 2004.
CAS Registry No. 832700-63-7, STN Entry Date Feb. 17, 2005.
Cignarella, G. et al., "Synthesis of a new series of 2,8-disubstituted-2,8-diazaspiro[4,5]decan-1-ones as potential muscarinic agonists", European Journal of Medicinal Chemistry, 1994, vol. 29, No. 12, pp. 955-961.
Fritch, P. C. et al., "Design, syntheses, and SAR of 2,8-diazaspiro[4.5]decanones as T-type calcium channel antagonists", Bioorganic & Medicinal Chemistry Letters, 2010, vol. 20, No. 22, pp. 6375-6378.
Süess, R. "165. Regiospezifische Reduktionen von 1,3,3-trisubstituierten Succinimiden mit Diboran", Helvetica Chimica Acta, 1977, vol. 60, No. 5, pp. 1650-1656.
U.S. Appl. No. 13/051,237, NMDA Receptor Modulators and Uses Thereof, filed Mar. 18, 2011, Abandoned, US 2011-0306586 Published on Dec. 15, 2011.
U.S. Appl. No. 14/050,641, NMDA Receptor Modulators and Uses Thereof, filed Oct. 10, 2013, Patented, U.S. Pat. No. 9,512,133 Issued Dec. 6, 2016.
U.S. Appl. No. 14/580,803, NMDA Receptor Modulators and Uses Thereof, filed Dec. 23, 2014, Patented, U.S. Pat. No. 9,802,946 Issued Oct. 31, 2017.
U.S. Appl. No. 15/785,603, NMDA Receptor Modulators and Uses Thereof, filed Oct. 17, 2017, Patented, U.S. Pat. No. 10,906,913 Issued on Feb. 2, 2021.
U.S. Appl. No. 17/111,657, NMDA Receptor Modulators and Uses Thereof, filed Dec. 4, 2020, Pending.
U.S. Appl. No. 16/006,125, Spiro-Lactam NMDA Modulators and Methods of Using Same, filed Jun. 12, 2018, Patented, U.S. Pat. No. 10,150,769 Issued on Dec. 11, 2018.
U.S. Appl. No. 16/197,584, Spiro-Lactam NMDA Modulators and Methods of Using Same, filed Nov. 21, 2018, Abandoned, US 2019-0330209 Published on Oct. 31, 2019.
U.S. Appl. No. 16/322,604, Spiro-Lactam NMDA Modulators and Methods of Using Same, filed Feb. 1, 2019, Published, US 2019-0194200 Published on Jun. 27, 2019.
U.S. Appl. No. 16/781,141, Spiro-Lactam NMDA Modulators and Methods of Using Same, filed Feb. 4, 2020, Published, US 2021-0002279 Published on Jan. 7, 2021.
U.S. Appl. No. 14/764,395, Spiro-Lactam NMDA Receptor Modulators and Uses Thereof, filed Jul. 29, 2015, Patented, U.S. Pat. No. 9,512,134 Issued Dec. 6, 2016.
U.S. Appl. No. 14/932,579, Spiro-Lactam Nmda Receptor Modulators and Uses Thereof, filed Nov. 4, 2015, Patented, U.S. Pat. No. 9,504,670 Issued Nov. 29, 2016.
U.S. Appl. No. 15/049,577, Spiro-Lactam NMDA Receptor Modulators and Uses Thereof, filed Feb. 22, 2016, Patented, U.S. Pat. No. 9,579,304 Issued Feb. 28, 2017.
U.S. Appl. No. 15/337,605, Spiro-Lactam NMDA Receptor Modulators and Uses Thereof, filed Oct. 28, 2016, Patented, U.S. Pat. No. 10,052,308 Issued on Aug. 21, 2018.
U.S. Appl. No. 15/969,186, Spiro-Lactam NMDA Receptor Modulators and Uses Thereof, filed May 2, 2018, Patented, U.S. Pat. No. 10,441,571 Issued Oct. 15, 2019.
U.S. Appl. No. 15/969,200, Spiro-Lactam NMDA Receptor Modulators and Uses Thereof, filed May 2, 2018, Patented, U.S. Pat. No. 10,441,572 Issued Oct. 15, 2019.
U.S. Appl. No. 16/536,582, Spiro-Lactum NMDA Receptor Modulators and Uses Thereof, filed Aug. 9, 2019, Patented, U.S. Pat. No. 11,077,094 Issued on Aug. 3, 2021.
U.S. Appl. No. 17/357,064, Spiro-Lactum NMDA Receptor Modulators and Uses Thereof, filed Jun. 24, 2021, Pending.
U.S. Appl. No. 14/764,402, Spiro-Lactum NMDA Receptor Modulators and Uses Thereof, filed Jul. 29, 2015, Patented U.S. Pat. No. 9,828,384 Issued Nov. 28, 2017.
U.S. Appl. No. 15/671,409, Spiro-Lactam NMDA Receptor Modulators and Uses Thereof, filed Aug. 8, 2017, Abandoned, US 2018-0179218 Published on Jun. 28, 2018.
U.S. Appl. No. 15/938,040, Spiro-Lactam NMDA Receptor Modulators and Uses Thereof, filed Mar. 28, 2018, Abandoned, US 2018-0215767 Published on Aug. 2, 2018.
U.S. Appl. No. 15/968,976, Spiro-Lactam NMDA Receptor Modulators and Uses Thereof, filed May 2, 2018, Abandoned US 2018-0244680 Published on Aug. 30, 2018.
U.S. Appl. No. 16/919,438, Spiro-Lactam NMDA Receptor Modulators and Uses Thereof, filed Jul. 2, 2020, Published, US 2021-0155632 Published on May 27, 2021.
U.S. Appl. No. 14/764,411, Spiro-Lactam NMDA Receptor Modulators and Uses Thereof, filed Jul. 29, 2015, U.S. Pat. No. 9,758,525 Issued Sep. 12, 2017.
U.S. Appl. No. 15/667,014, Spiro-Lactam NMDA Receptor Modulators and Uses Thereof, filed Aug. 2, 2017, Patented, U.S. Pat. No. 10,273,239 Issued Apr. 30, 2019.
U.S. Appl. No. 14/764,419, Spiro-Lactam NMDA Receptor Modulators and Uses Thereof, filed Jul. 29, 2015, Patented, U.S. Pat. No. 9,738,650 Issued Aug. 22, 2017.
U.S. Appl. No. 15/653,738, Spiro-Lactam NMDA Receptor Modulators and Uses Thereof, filed Jul. 19, 2017, Patented, U.S. Pat. No. 10,253,032 Issued Apr. 9, 2019.
U.S. Appl. No. 14/764,426, Spiro-Lactam NMDA Receptor Modulators and Uses Thereof, filed Jul. 29, 2015, Patented, U.S. Pat. No. 9,708,335 Issued Jul. 18, 2017.
U.S. Appl. No. 15/625,163, Spiro-Lactam NMDA Receptor Modulators and Uses Thereof, filed Jun. 16, 2017, Patented, U.S. Pat. No. 10,316,041 Issued Jun. 11, 2019.
U.S. Appl. No. 16/321,901, Spiro-Lactam NMDA Receptor Modulators and Uses Thereof, filed Jan. 30, 2019, Patented, U.S. Pat. No. 10,961,189 Issued on Mar. 30, 2021.
U.S. Appl. No. 17/177,336, Spiro-Lactam NMDA Receptor Modulators and Uses Thereof, filed Feb. 17, 2021, Pending.
U.S. Appl. No. 16/321,903, Spiro-Lactam NMDA Receptor Modulators and Uses Thereof, filed Jan. 30, 2019, Patented, U.S. Pat. No. 10,918,637 Issued on Feb. 16, 2021.
U.S. Appl. No. 17/108,199, Spiro-Lactam NMDA Receptor Modulators and Uses Thereof, filed Dec. 1, 2020, Pending, US 2021-0322406 Published on Oct. 21, 2021.
U.S. Appl. No. 16/505,947, Methods of Identifying Compounds for Treating Depression and Other Related Diseases, filed Jul. 9, 2019, Abandoned.
U.S. Appl. No. 16/321,906, Spiro-Lactam and Bis-Spiro-Lactam NMDA Receptor Modulators and Uses Thereof, filed Jan. 30, 2019, Published, U.S. Pat. No. 11,028,095 Issued on Jun. 8, 2021.
U.S. Appl. No. 17/314,174, Spiro-Lactam and Bis-Spiro-Lactam NMDA Receptor Modulators and Uses Thereof, filed May 7, 2021 Pending.
U.S. Appl. No. 15/638,669, Spiro-Lactam NMDA Receptor Modulators and Uses Thereof, filed Jun. 30, 2017, Patented, U.S. Pat. No. 9,932,347 Issued Apr. 3, 2018.
U.S. Appl. No. 15/830,378, Spiro-Lactam NMDA Receptor Modulators and Uses Thereof, filed Dec. 4, 2017, Patented, U.S. Pat. No. 10,196,401 Issued on Feb. 5, 2019.
U.S. Appl. No. 16/225,538, Spiro-Lactam NMDA Receptor Modulators and Uses Thereof, filed Dec. 19, 2018, Abandoned.
U.S. Appl. No. 15/636,888, Spiro-Lactam NMDA Receptor Modulators and Uses Thereof, filed Jun. 29, 2017, Patented, U.S. Pat. No. 9,925,169 Issued Mar. 27, 2018.
U.S. Appl. No. 15/830,383, Spiro-Lactam Nmda Receptor Modulators and Uses Thereof, filed Dec. 4, 2017, Patented, U.S. Pat. No. 10,195,179 Issued on Feb. 5, 2019.
U.S. Appl. No. 16/966,176, Spiro-Lactam NMDA Receptor Modulators and Uses Thereof, filed Jul. 30, 2020, Published, US 2021-0047324 Published on Feb. 18, 2021.

(56) References Cited

OTHER PUBLICATIONS

U.S. Appl. No. 16/966,170, Spiro-Lactam NMDA Receptor Modulators and Uses Thereof, filed Jul. 30, 2020, Published, US 2021-0040095 Published on Feb. 11, 2021.
U.S. Appl. No. 17/094,584, Methods of Treating Painful Diabetic Peripheral Neuropathy, filed Nov. 10, 2020, Published US 2021-0139489 Published on May 13, 2021.
U.S. Appl. No. 17/094,595, Methods of Treating Fibromyalgia, filed Nov. 10, 2020, Pending, US 2021-0308101 Published on Oct. 7, 2021.
U.S. Appl. No. 17/110,481, Methods of Treating Cognitive Impairment Associated with Neurodegenerative Disease, filed Dec. 3, 2020, Pending, US 2021-0322393 Published on Oct. 21, 2021.

* cited by examiner

SPIRO-LACTAM NMDA RECEPTOR MODULATORS AND USES THEREOF

This application is a national stage application under 35 U.S.C. § 371 of International Application No. PCT/US2017/044838, filed on Aug. 1, 2017, which application claims priority to and the benefit of U.S. Provisional Patent Application No. 62/369,453, filed on Aug. 1, 2016; the contents of each of which are hereby incorporated by reference herein in their entirety.

BACKGROUND

An N-methyl-d-aspartate ("NMDA") receptor is a post-synaptic, ionotropic receptor that is responsive to, inter alia, the excitatory amino acids glutamate and glycine and the synthetic compound NMDA. The NMDA receptor controls the flow of both divalent and monovalent ions into the postsynaptic neural cell through a receptor associated channel (Foster et al., Nature 1987, 329:395-396; Mayer et al., Trends in Pharmacol. Sci. 1990, 11:254-260). The NMDA receptor has been implicated during development in specifying neuronal architecture and synaptic connectivity, and may be involved in experience-dependent synaptic modifications. In addition, NMDA receptors are also thought to be involved in long term potentiation and central nervous system disorders.

The NMDA receptor plays a major role in the synaptic plasticity that underlies many higher cognitive functions, such as memory acquisition, retention and learning, as well as in certain cognitive pathways and in the perception of pain (Collingridge et al., The NMDA Receptor, Oxford University Press, 1994). In addition, certain properties of NMDA receptors suggest that they may be involved in the information-processing in the brain that underlies consciousness itself.

The NMDA receptor has drawn particular interest since it appears to be involved in a broad spectrum of CNS disorders. For instance, during brain ischemia caused by stroke or traumatic injury, excessive amounts of the excitatory amino acid glutamate are released from damaged or oxygen deprived neurons. This excess glutamate binds to the NMDA receptors which opens their ligand-gated ion channels; in turn the calcium influx produces a high level of intracellular calcium which activates a biochemical cascade resulting in protein degradation and cell death. This phenomenon, known as excitotoxicity, is also thought to be responsible for the neurological damage associated with other disorders ranging from hypoglycemia and cardiac arrest to epilepsy. In addition, there are preliminary reports indicating similar involvement in the chronic neurodegeneration of Huntington's, Parkinson's and Parkinson's related conditions such as dyskinesia and L-dopa induced dyskinesia and Alzheimer's diseases. Activation of the NMDA receptor has been shown to be responsible for post-stroke convulsions, and, in certain models of epilepsy, activation of the NMDA receptor has been shown to be necessary for the generation of seizures. Neuropsychiatric involvement of the NMDA receptor has also been recognized since blockage of the NMDA receptor $Ca^{++}$ channel by the animal anesthetic PCP (phencyclidine) produces a psychotic state in humans similar to schizophrenia (reviewed in Johnson, K. and Jones, S., 1990). Further, NMDA receptors have also been implicated in certain types of spatial learning.

The NMDA receptor is believed to consist of several protein chains embedded in the postsynaptic membrane. The first two types of subunits discovered so far form a large extracellular region, which probably contains most of the allosteric binding sites, several transmembrane regions looped and folded so as to form a pore or channel, which is permeable to $Ca^{++}$, and a carboxyl terminal region. The opening and closing of the channel is regulated by the binding of various ligands to domains (allosteric sites) of the protein residing on the extracellular surface. The binding of the ligands is thought to affect a conformational change in the overall structure of the protein which is ultimately reflected in the channel opening, partially opening, partially closing, or closing.

A need continues to exist in the art for novel and more specific and/or potent compounds that are capable of modulating NMDA receptors, and provide pharmaceutical benefits. In addition, a need continues to exist in the medical arts for orally deliverable forms of such compounds.

SUMMARY

The present disclosure includes compounds that can be NMDA modulators. More specifically, the present disclosure provides a compound having the formula:

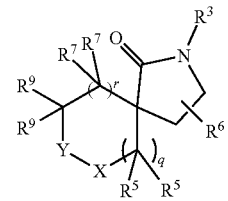

or a pharmaceutically acceptable salt and/or a stereoisomer thereof, wherein:
  X is $NR^1$ or $CR^2R^2$;
  Y is $NR^1$ or $CR^2R^2$, wherein one of X or Y is $NR^1$;
  $R^1$ is selected from the group consisting of H, $C_1$-$C_6$alkyl, phenyl, —C(O)—$C_1$-$C_6$alkyl, and —C(O)—O—$C_1$-$C_6$ alkyl;
  q is 0 or 1;
  r is 1 or 2;
  $R^7$ is independently selected from the group consisting of H, —$C_1$-$C_6$alkyl, —S(O)$_w$—$C_1$-$C_3$alkyl, and halogen;
  $R^9$ is independently selected from the group consisting of H, —$C_1$-$C_6$alkyl, —S(O)$_w$—$C_1$-$C_3$alkyl, and halogen, or $R^7$ and $R^9$ taken together with the adjacent carbons to which they are attached form a 3-membered carbocyclic ring which can be optionally substituted by one or two substituents independently selected from the group consisting of halogen, hydroxyl, —$C_1$-$C_3$alkyl, —$C_1$-$C_3$alkoxy, —C(O)$NR^aR^b$, and —$NR^aR^b$;
  $R^2$ is independently selected for each occurrence from the group consisting of H, $C_1$-$C_6$alkyl, —S(O)$_w$—$C_1$-$C_3$alkyl, —$NR^aR^b$ and halogen;
  $R^5$ is independently selected for each occurrence from the group consisting of H, $C_1$-$C_6$alkyl, —S(O)$_w$—$C_1$-$C_3$alkyl, —$NR^aR^b$ and halogen;
  $R^6$ represents one or two optional substitutions each on one or more available ring carbons, and is independently selected for each occurrence from the group consisting of $C_1$-$C_6$alkyl, —S(O)$_w$—$C_1$-$C_3$alkyl, —$NR^aR^b$ and halogen;
  w is 0, 1, or 2;
  $R^3$ is selected from the group consisting of H, phenyl, $C_1$-$C_6$ alkyl, —C(O)$R^{31}$ and —C(O)$OR^{32}$;

$R^{31}$ and $R^{32}$ are each independently H, $C_1$-$C_6$alkyl, —$C_3$-$C_6$cycloalkyl, and phenyl; and $R^a$ and $R^b$ are each independently for each occurrence selected from the group consisting of H, phenyl, and $C_1$-$C_3$alkyl, or $R^a$ and $R^b$ taken together with the nitrogen to which they are attached form a 4-6 membered heterocyclic ring;

wherein any aforementioned $C_1$-$C_6$ alkyl, independently for each occurrence, can be optionally substituted by one, two or three substituents each independently selected from —C(O)NR$^a$R$^b$, —NR$^a$R$^b$, hydroxyl, S(O)$_w$—$C_1$-$C_3$alkyl, SH, phenyl and halogen, and any aforementioned phenyl, independently for each occurrence, can be optionally substituted by one, two or three substituents each independently selected from —C(O)—$C_1$-$C_3$alkyl, hydroxyl, —C(O)— $C_1$-$C_3$alkyl, methyl, CF$_3$ and halogen.

Also provided herein are pharmaceutically acceptable compositions comprising a disclosed compound, and a pharmaceutically acceptable excipient. Such compositions can be suitable for administration to a patient orally, parenterally, topically, intravaginally, intrarectally, sublingually, ocularly, transdermally, or nasally.

In some aspects, compounds described herein bind to NMDA receptors expressing certain NR2 subtypes. In some aspects, the compounds described herein bind to one NR2 subtype and not another.

In another aspect, a method of treating a condition selected from the group consisting of autism, anxiety, depression, bipolar disorder, attention deficit disorder, attention deficit hyperactivity disorder (ADHD), schizophrenia, a psychotic disorder, a psychotic symptom, social withdrawal, obsessive-compulsive disorder, phobia, post-traumatic stress syndrome, a behavior disorder, an impulse control disorder, a substance abuse disorder, a sleep disorder, a memory disorder, a learning disorder, urinary incontinence, multiple system atrophy, progressive supra-nuclear palsy, Friedrich's ataxia, Down's syndrome, fragile X syndrome, tuberous sclerosis, olivio-ponto-cerebellar atrophy, Rett syndrome, cerebral palsy, drug-induced optic neuritis, ischemic retinopathy, diabetic retinopathy, glaucoma, dementia, AIDS dementia, Alzheimer's disease, Huntington's chorea, spasticity, myoclonus, muscle spasm, Tourette's syndrome, epilepsy, cerebral ischemia, stroke, a brain tumor, traumatic brain injury, cardiac arrest, myelopathy, spinal cord injury, peripheral neuropathy, fibromyalgia, acute neuropathic pain, and chronic neuropathic pain, in a patient in need thereof is provided. Such methods may comprise administering to the patient a pharmaceutically effective amount of a disclosed compound or pharmaceutically acceptable salts, stereoisomers, N-oxides, and hydrates thereof.

In some embodiments, a method of the disclosure includes treating neuropathic pain, wherein the neuropathic pain is selected from the group consisting of herpes, HIV, traumatic nerve injury, stroke, post-ischemia, chronic back pain, post-herpetic neuralgia, fibromyalgia, reflex sympathetic dystrophy, complex regional pain syndrome, spinal cord injury, sciatica, phantom limb pain, diabetic neuropathy, and cancer chemotherapeutic-induced neuropathic pain.

In some embodiments, a method of the disclosure includes treating depression. For example, depression may include one or more of major depressive disorder, dysthymic disorder, psychotic depression, postpartum depression, seasonal affective disorder, bipolar disorder, mood disorder, or depression caused by a chronic medical condition. In certain embodiments, a disclosed method may treat schizophrenia. Such schizophrenia may be, for example, paranoid type schizophrenia, disorganized type schizophrenia, catatonic type schizophrenia, undifferentiated type schizophrenia, residual type schizophrenia, post-schizophrenic depression, or simple schizophrenia.

DETAILED DESCRIPTION

This disclosure is generally directed to compounds that are capable of modulating NMDA receptors, for example, NMDA receptor antagonists, agonists, or partial agonists, and compositions and/or methods of using the disclosed compounds. It should be appreciated that the disclosed compounds may modulate other protein targets and/or specific NMDA receptor subtype.

The term "alkyl," as used herein, refers to a saturated straight-chain or branched hydrocarbon, such as a straight-chain or branched group of 1-6, 1-4, or 1-3 carbon atoms, referred to herein as $C_1$-$C_6$ alkyl, $C_1$-$C_4$ alkyl, and $C_1$-$C_3$ alkyl, respectively. For example, "$C_1$-$C_6$ alkyl" refers to a straight-chain or branched saturated hydrocarbon containing 1-6 carbon atoms. Examples of a $C_1$-$C_6$ alkyl group include, but are not limited to, methyl, ethyl, propyl, butyl, pentyl, hexyl, isopropyl, isobutyl, sec-butyl, tert-butyl, isopentyl, and neopentyl. In another example, "$C_1$-$C_4$ alkyl" refers to a straight-chain or branched saturated hydrocarbon containing 1-4 carbon atoms. Examples of a $C_1$-$C_4$ alkyl group include, but are not limited to, methyl, ethyl, propyl, butyl, isopropyl, isobutyl, sec-butyl and tert-butyl. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 3-methyl-2-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl.

The term "alkoxy," as used herein, refers to an alkyl group attached to an oxygen atom (alkyl-O—). Alkoxy groups can have 1-6 or 2-6 carbon atoms and are referred to herein as $C_1$-$C_6$ alkoxy and $C_2$-$C_6$ alkoxy, respectively. Exemplary alkoxy groups include, but are not limited to, methoxy, ethoxy, propyloxy, isopropoxy, and tert-butoxy.

The term "carbonyl," as used herein, refers to the radical —C(O)— or C=O.

The term "cyano," as used herein, refers to the radical —CN.

The phrase, "carbocyclic ring," as used herein, refers to a hydrocarbon ring system in which all the ring atoms are carbon. Exemplary carbocyclic rings including cycloalkyls and phenyl.

The term "cycloalkyl," as used herein, refers to a monocyclic saturated or partially unsaturated hydrocarbon ring (carbocyclic) system, for example, where each ring is either completely saturated or contains one or more units of unsaturation, but where no ring is aromatic. A cycloalkyl can have 3-6 or 4-6 carbon atoms in its ring system, referred to herein as $C_3$-$C_6$ cycloalkyl or $C_4$-$C_6$ cycloalkyl, respectively. Exemplary cycloalkyl groups include, but are not limited to, cyclohexyl, cyclohexenyl, cyclopentyl, cyclopentenyl, cyclobutyl, and cyclopropyl.

The terms "halo" and "halogen," as used herein, refer to fluoro (F), chloro (Cl), bromo (Br), and/or iodo (I).

The term "heteroatom," as used herein, refers to an atom of any element other than carbon or hydrogen and includes, for example, nitrogen (N), oxygen (O), silicon (Si), sulfur (S), phosphorus (P), and selenium (Se).

The term "heterocyclic ring" or "heterocycloalkyl," as used herein, is art-recognized and refer to saturated or partially unsaturated 3- to 8-membered ring structures, whose ring system include one, two or three heteroatoms, such as nitrogen, oxygen, and/or sulfur. A heterocyclic ring can be fused to one or more phenyl, partially unsaturated, or saturated rings. Examples of heterocyclic ring include, but are not limited to, pyrrolidinyl, piperidinyl, morpholinyl, thiomorpholinyl, and piperazinyl.

The terms "hydroxy" and "hydroxyl," as used herein, refer to the radical —OH.

The term "oxo," as used herein, refers to the radical =O (double bonded oxygen).

The term "amino acid," as used herein, includes any one of the following alpha amino acids: isoleucine, alanine, leucine, asparagine, lysine, aspartate, methionine, cysteine, phenylalanine, glutamate, threonine, glutamine, tryptophan, glycine, valine, proline, arginine, serine, histidine, and tyrosine. An amino acid also can include other art-recognized amino acids such as beta amino acids.

The term "compound," as used herein, refers to the compound itself and its pharmaceutically acceptable salts, hydrates, esters and N-oxides including its various stereoisomers and its isotopically-labelled forms, unless otherwise understood from the context of the description or expressly limited to one particular form of the compound, i.e., the compound itself, a specific stereoisomer and/or isotopically-labelled compound, or a pharmaceutically acceptable salt, a hydrate, an ester, or an N-oxide thereof. It should be understood that a compound can refer to a pharmaceutically acceptable salt, or a hydrate, an ester or an N-oxide of a stereoisomer of the compound and/or an isotopically-labelled compound.

The compounds of the disclosure can contain one or more chiral centers and/or double bonds and therefore, can exist as stereoisomers, such as geometric isomers, and enantiomers or diastereomers. The term "stereoisomers," when used herein, consists of all geometric isomers, enantiomers and/or diastereomers of the compound. For example, when a compound is shown with specific chiral center(s), the compound depicted without such chirality at that and other chiral centers of the compound are within the scope of the present disclosure, i.e., the compound depicted in two-dimensions with "flat" or "straight" bonds rather than in three dimensions, for example, with solid or dashed wedge bonds. Stereospecific compounds may be designated by the symbols "R" or "S," depending on the configuration of substituents around the stereogenic carbon atom. The present disclosure encompasses all the various stereoisomers of these compounds and mixtures thereof. Mixtures of enantiomers or diastereomers can be designated "(±)" in nomenclature, but a skilled artisan will recognize that a structure can denote a chiral center implicitly. It is understood that graphical depictions of chemical structures, e.g., generic chemical structures, encompass all stereoisomeric forms of the specified compounds, unless indicated otherwise.

Individual enantiomers and diastereomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns, or (4) kinetic resolution using stereoselective chemical or enzymatic reagents. Racemic mixtures also can be resolved into their component enantiomers by well-known methods, such as chiral-phase gas chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations. See, for example, Carreira and Kvaerno, *Classics in Stereoselective Synthesis*, Wiley-VCH: Weinheim, 2009.

Geometric isomers, resulting from the arrangement of substituents around a carbon-carbon double bond or arrangement of substituents around a cycloalkyl or heterocycloalkyl, can also exist in the compounds of the present disclosure. The symbol ═══ denotes a bond that may be a single, double or triple bond as described herein. Substituents around a carbon-carbon double bond are designated as being in the "Z" or "E" configuration, where the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The disclosure also embraces isotopically-labeled compounds which are identical to those compounds recited herein, except that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorus, fluorine and chlorine, such as $^2H$ ("D"), $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound described herein can have one or more H atoms replaced with deuterium.

Certain isotopically-labeled compounds (e.g., those labeled with $^3H$ and $^{14}C$) can be useful in compound and/or substrate tissue distribution assays. Tritiated (i.e., $^3H$) and carbon-14 (i.e., $^{14}C$) isotopes can be particularly preferred for their ease of preparation and detectability. Further, substitution with heavier isotopes such as deuterium (i.e., $^2H$) can afford certain therapeutic advantages resulting from greater metabolic stability (e.g., increased in vivo half-life or reduced dosage requirements) and hence can be preferred in some circumstances. Isotopically-labeled compounds can generally be prepared by following procedures analogous to those disclosed herein, for example, in the Examples section, by substituting an isotopically-labeled reagent for a non-isotopically-labeled reagent.

The phrases "pharmaceutically acceptable" and "pharmacologically acceptable," as used herein, refer to compounds, molecular entities, compositions, materials, and/or dosage forms that do not produce an adverse, allergic or other untoward reaction when administered to an animal, or a human, as appropriate. For human administration, preparations should meet sterility, pyrogenicity, general safety and purity standards as required by FDA Office of Biologics standards.

The phrases "pharmaceutically acceptable carrier" and "pharmaceutically acceptable excipient," as used herein, refer to any and all solvents, dispersion media, coatings, isotonic and absorption delaying agents, and the like, that are compatible with pharmaceutical administration. Pharmaceutical acceptable carriers can include phosphate buffered saline solution, water, emulsions (e.g., such as an oil/water or water/oil emulsions), and various types of wetting agents. The compositions also can include stabilizers and preservatives.

The phrase "pharmaceutical composition," as used herein, refers to a composition comprising at least one compound as disclosed herein formulated together with one or more pharmaceutically acceptable carriers. The pharmaceutical compositions can also contain other active compounds providing supplemental, additional, or enhanced therapeutic functions.

The terms "individual," "patient," and "subject," as used herein, are used interchangeably and include any animal, including mammals, preferably mice, rats, other rodents, rabbits, dogs, cats, swine, cattle, sheep, horses, or primates, and more preferably, humans. The compounds described in the disclosure can be administered to a mammal, such as a human, but can also be administered to other mammals such as an animal in need of veterinary treatment, for example, domestic animals (e.g., dogs, cats, and the like), farm animals (e.g., cows, sheep, pigs, horses, and the like) and laboratory animals (e.g., rats, mice, guinea pigs, and the like). The mammal treated in the methods described in the disclosure is preferably a mammal in which treatment, for example, of pain or depression, is desired.

The term "treating," as used herein, includes any effect, for example, lessening, reducing, modulating, ameliorating, or eliminating, that results in the improvement of the condition, disease, disorder, and the like, including one or more symptoms thereof. Treating can be curing, improving, or at least partially ameliorating the disorder.

The term "disorder" refers to and is used interchangeably with, the terms "disease," "condition," or "illness," unless otherwise indicated.

The term "modulation," as used herein, refers to and includes antagonism (e.g., inhibition), agonism, partial antagonism, and/or partial agonism.

The phrase "therapeutically effective amount," as used herein, refers to the amount of a compound (e.g., a disclosed compound) that will elicit the biological or medical response of a tissue, system, animal or human that is being sought by the researcher, veterinarian, medical doctor or other clinician. The compounds described in the disclosure can be administered in therapeutically effective amounts to treat a disease. A therapeutically effective amount of a compound can be the quantity required to achieve a desired therapeutic and/or prophylactic effect, such as an amount which results in lessening of a symptom of a disease such as depression.

As used herein, the term "pharmaceutically acceptable salt" refers to any salt of an acidic or a basic group that may be present in a compound of the present disclosure, which salt is compatible with pharmaceutical administration. As is known to those of skill in the art, "salts" of the compounds of the present disclosure may be derived from inorganic or organic acids and bases.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present disclosure compounded with a suitable cation such as $Na^+$, $NH_4^+$, and $NW_4^+$ (where W can be a $C_{1-4}$ alkyl group), and the like. For therapeutic use, salts of the compounds of the present disclosure can be pharmaceutically acceptable. However, salts of acids and bases that are non-pharmaceutically acceptable may also find use, for example, in the preparation or purification of a pharmaceutically acceptable compound.

Compounds included in the present compositions that are basic in nature are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions, including but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts.

Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

Compounds included in the present compositions that include a basic or acidic moiety can also form pharmaceutically acceptable salts with various amino acids. The compounds of the disclosure can contain both acidic and basic groups; for example, one amino and one carboxylic acid group. In such a case, the compound can exist as an acid addition salt, a zwitterion, or a base salt.

The compounds disclosed herein can exist in a solvated form as well as an unsolvated form with pharmaceutically acceptable solvents such as water, ethanol, and the like, and it is intended that the disclosure embrace both solvated and unsolvated forms. In some embodiments, the compound is amorphous. In certain embodiments, the compound is a single polymorph. In various embodiments, the compound is a mixture of polymorphs. In particular embodiments, the compound is in a crystalline form.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al, Nature Reviews Drug Discovery 2008, 7, 255). For example, if a compound described herein or a pharmaceutically acceptable salt, hydrate or solvate of the compound contains a carboxylic acid functional group, a prodrug can comprise an ester formed by the replacement of the hydrogen atom of the acid group with a group such as $(C_1-C_8)$alkyl, $(C_2-C_{12})$ alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$alkyl.

Similarly, if a compound described herein contains an alcohol functional group, a prodrug can be formed by the replacement of the hydrogen atom of the alcohol group with a group such as $(C_1-C_6)$alkanoyloxymethyl, 1-($(C_1-C_6)$alkanoyloxy)ethyl, 1-methyl-1-($(C_1-C_6)$alkanoyloxy)ethyl $(C_1-C_6)$alkoxycarbonyloxymethyl, N—$(C_1-C_6)$alkoxycarbonylaminomethyl, succinoyl, $(C_1-C_6)$alkanoyl, α-amino $(C_1-C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate).

If a compound described herein incorporates an amine functional group, a prodrug can be formed, for example, by creation of an amide or carbamate, an N-acyloxyakyl derivative, an (oxodioxolenyl) methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplício, et al., *Molecules* 2008, 13, 519 and references therein.

Unless defined otherwise, all technical and scientific terms used herein have the same meaning as commonly understood by one of ordinary skill in the art to which this disclosure pertains.

Throughout the description, where compositions and kits are described as having, including, or comprising specific components, or where processes and methods are described as having, including, or comprising specific steps, it is contemplated that, additionally, there are compositions and kits of the present disclosure that consist essentially of, or consist of, the recited components, and that there are processes and methods according to the present disclosure that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present disclosure, whether explicit or implicit herein. For example, where reference is made to a particular compound, that compound can be used in various embodiments of compositions of the present disclosure and/or in methods of the present disclosure, unless otherwise understood from the context. In other words, within this application, embodiments have been described and depicted in a way that enables a clear and concise application to be written and drawn, but it is intended and will be appreciated that embodiments can be variously combined or separated without parting from the present teachings and disclosure(s). For example, it will be appreciated that all features described and depicted herein can be applicable to all aspects of the disclosure(s) described and depicted herein.

The articles "a" and "an" are used in this disclosure to refer to one or more than one (i.e., to at least one) of the grammatical object of the article, unless the context is inappropriate. By way of example, "an element" means one element or more than one element.

The term "and/or" is used in this disclosure to mean either "and" or "or" unless indicated otherwise.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present disclosure also include the specific quantitative value itself, unless specifically stated otherwise. As used herein, the term "about" refers to a ±10% variation from the nominal value unless otherwise indicated or inferred.

Where a percentage is provided with respect to an amount of a component or material in a composition, the percentage should be understood to be a percentage based on weight, unless otherwise stated or understood from the context.

Where a molecular weight is provided and not an absolute value, for example, of a polymer, then the molecular weight should be understood to be an average molecule weight, unless otherwise stated or understood from the context.

It should be understood that the order of steps or order for performing certain actions is immaterial so long as the present disclosure remain operable. Moreover, two or more steps or actions can be conducted simultaneously.

At various places in the present specification, substituents are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1-C_6$, $C_1-C_5$, $C_1-C_4$, $C_1-C_3$, $C_1-C_2$, $C_2-C_6$, $C_2-C_5$, $C_2-C_4$, $C_2-C_3$, $C_3-C_6$, $C_3-C_5$, $C_3-C_4$, $C_4-C_6$, $C_4-C_5$, and $C_5-C_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

Additional examples include that the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4, and 4-5 substituents.

The use of any and all examples, or exemplary language herein, for example, "such as" or "including," is intended merely to illustrate better the present disclosure and does not pose a limitation on the scope of the disclosure unless claimed. No language in the specification should be construed as indicating any non-claimed element as essential to the practice of the present disclosure.

Further, if a variable is not accompanied by a definition, then the variable is defined as found elsewhere in the disclosure unless understood to be different from the context. In addition, the definition of each variable and/or substituent, for example, $C_1$-$C_6$ alkyl, $R^2$, $R^b$, w and the like, when it occurs more than once in any structure or compound, can be independent of its definition elsewhere in the same structure or compound.

Definitions of the variables and/or substituents in formulae and/or compounds herein encompass multiple chemical groups. The present disclosure includes embodiments where, for example, i) the definition of a variable and/or substituent is a single chemical group selected from those chemical groups set forth herein, ii) the definition is a collection of two or more of the chemical groups selected from those set forth herein, and iii) the compound is defined by a combination of variables and/or substituents in which the variables and/or substituents are defined by (i) or (ii).

Various aspects of the disclosure are set forth herein under headings and/or in sections for clarity; however, it is understood that all aspects, embodiments, or features of the disclosure described in one particular section are not to be limited to that particular section but rather can apply to any aspect, embodiment, or feature of the present disclosure.

Compounds

Disclosed compounds include a compound having the formula:

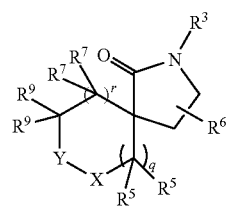

or a pharmaceutically acceptable salt and/or stereoisomer thereof, wherein:

X is $NR^1$ or $CR^2R^2$;
Y is $NR^1$ or $CR^2R^2$, wherein one of X or Y is $NR^1$;
$R^1$ is selected from the group consisting of H, $C_1$-$C_6$alkyl, phenyl, —C(O)—$C_1$-$C_6$alkyl, and —C(O)—O—$C_1$-$C_6$ alkyl;
q is 0 or 1;
r is 1 or 2;
$R^7$ is independently selected from the group consisting of H, —$C_1$-$C_6$alkyl, —$S(O)_w$—$C_1$-$C_3$alkyl, cyano, and halogen;
$R^9$ is independently selected from the group consisting of H, —$C_1$-$C_6$alkyl, —$S(O)_w$—$C_1$-$C_3$alkyl, cyano, and halogen, or $R^7$ and $R^9$ taken together with the adjacent carbons to which they are attached form a 3-membered carbocyclic ring which can be optionally substituted by one or two substituents independently selected from the group consisting of halogen, hydroxyl, —$C_1$-$C_3$alkyl, —$C_1$-$C_3$alkoxy, —$C(O)NR^aR^b$, and —$NR^aR^b$;

$R^2$ is independently selected for each occurrence from the group consisting of H, $C_1$-$C_6$alkyl, —$S(O)_w$—$C_1$-$C_3$alkyl, —$NR^aR^b$ and halogen;

$R^5$ is independently selected for each occurrence from the group consisting of H, $C_1$-$C_6$alkyl, —$S(O)_w$—$C_1$-$C_3$alkyl, $NR^aR^b$, cyano and halogen;

$R^6$ represents one or two optional substitutions each on one or more available ring carbons, and is independently selected for each occurrence from the group consisting of $C_1$-$C_6$alkyl, —$S(O)_w$—$C_1$-$C_3$alkyl, —$NR^aR^b$ and halogen;

w is 0, 1, or 2;

$R^3$ is selected from the group consisting of H, phenyl, $C_1$-$C_6$ alkyl, —$C(O)R^{31}$ and —$C(O)OR^{32}$;

$R^{31}$ and $R^{32}$ are each independently H, $C_1$-$C_6$alkyl, —$C_3$-$C_6$cycloalkyl, and phenyl; and $R^a$ and $R^b$ are each independently for each occurrence selected from the group consisting of H, phenyl, and $C_1$-$C_3$alkyl, or $R^a$ and $R^b$ taken together with the nitrogen to which they are attached form a 4-6 membered heterocyclic ring;

wherein any aforementioned $C_1$-$C_6$ alkyl, independently for each occurrence, can be optionally substituted by one, two or three substituents each independently selected from —$C(O)NR^aR^b$, —$NR^aR^b$, hydroxyl, $S(O)_w$—$C_1$-$C_3$alkyl (where w is 0, 1, or 2), SH, phenyl and halogen, and any aforementioned phenyl, independently for each occurrence, can be optionally substituted by one, two or three substituents each independently selected from —$C(O)$—$C_1$-$C_3$alkyl, hydroxyl, —$C(O)$— $C_1$-$C_3$alkyl, methyl, $CF_3$ and halogen.

In some embodiments, q can be 1. In certain embodiments, q can be 0. In some embodiments, q can be 0 and r can be 2.

In some embodiments, X can be $NR^1$ and Y can be $CR^2R^2$. In certain embodiments, $R^1$ can be C(O)—O—$C_1$-$C_6$ alkyl, —C(O)—$C_1$-$C_6$alkyl, $C_1$-$C_6$alkyl, or H.

In various embodiments, a disclosed compound has the formula:

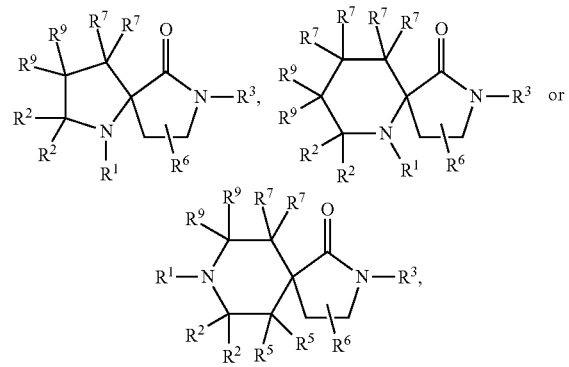

or a pharmaceutically acceptable salt and/or a stereoisomer thereof, where the variables $R^1$, $R^2$, $R^3$, $R^5$, $R^6$, $R^7$, and $R^9$ are as defined herein.

In some embodiments, $R^1$ can be C(O)—$C_1$-$C_6$alkyl, where C(O)—$C_1$-$C_6$alkyl can be represented by:

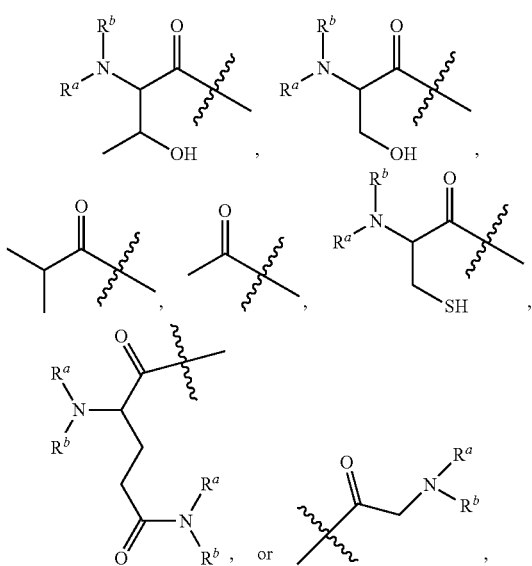

wherein $R^a$ and $R^b$ can be each independently selected for each occurrence from the group consisting of hydrogen and —$C_1$-$C_6$alkyl.

In some embodiments, $R^1$ can be $C_1$-$C_6$alkyl. For example, $R^1$ can be

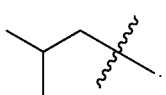 [SMILES: *CC(C)C]

In some embodiments, $R^1$ can be C(O)—O—$C_1$-$C_6$ alkyl. For example, $R^1$ can be tert-butyloxycarbonyl.

In some embodiments, $R^3$ can be H. In certain embodiments, $R^3$ can be selected from the group consisting of:

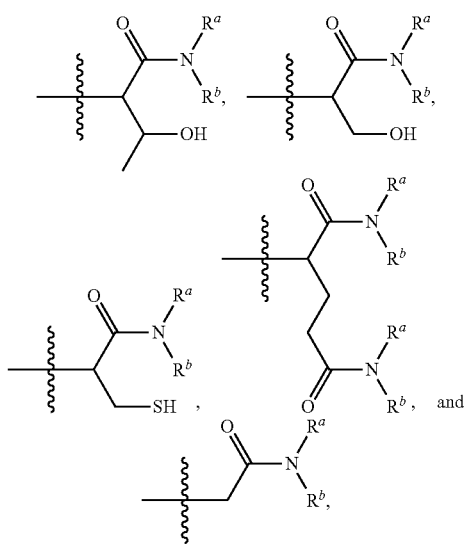

wherein $R^a$ and $R^b$ can be each independently selected for each occurrence from the group consisting of hydrogen and —$C_1$-$C_6$alkyl.

In certain embodiments, $R^1$ and/or $R^3$ independently can be an amino acid or a derivative of an amino acid, for example, an alpha "amino amide" represented by $H_2N$—CH(amino acid side chain)-C(O)$NH_2$. In certain embodiments, the nitrogen atom of the amino group of the amino acid or the amino acid derivative is a ring nitrogen in a chemical formula described herein. In such embodiments, the carboxylic acid of the amino acid or the amide group of an amino amide (amino acid derivative) is not within the ring structure, i.e., not a ring atom. In certain embodiments, the carboxylic acid group of the amino acid or the amino acid derivative forms an amide bond with a ring nitrogen in a chemical formula disclosed herein, thereby providing an amino amide, where the amino group of the amino amide is not within the ring structure, i.e., not a ring atom. In certain embodiments, $R^1$ and/or $R^3$ independently can be an alpha amino acid, an alpha amino acid derivative, and/or another amino acid or amino acid derivative such as a beta amino acid or a beta amino acid derivative, for example, a beta amino amide.

In various embodiments, $R^2$ is H at each occurrence. In some embodiments, $R^5$ is H at each occurrence. In certain embodiments, $R^6$ is H. In particular embodiments, $R^7$ is H at each occurrence. In some embodiments, $R^9$ is H at each occurrence.

In some embodiments, a disclosed compound is selected from the compounds delineated in the Examples, and includes pharmaceutically acceptable salts and/or stereoisomers thereof.

In certain embodiments, a disclosed compound includes one having the formula selected from the group consisting of:

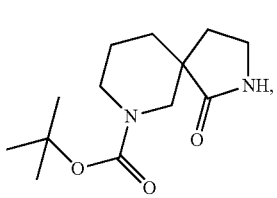
RE-1

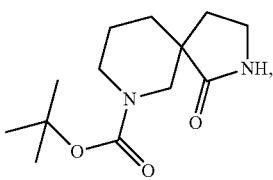
RA-1

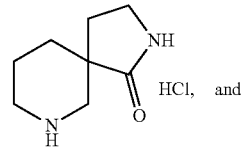
RB-1

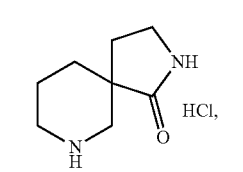
RB-1 or a pharmaceutically acceptable salt or a stereoisomer thereof.

In certain embodiments, a disclosed compound includes one having the formula selected from the group consisting of:

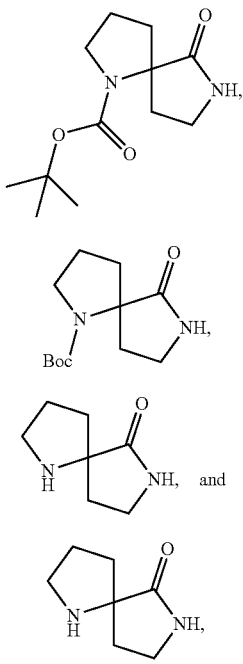

or a pharmaceutically acceptable salt or a stereoisomer thereof.

The compounds of the present disclosure and formulations thereof may have a plurality of chiral centers. Each chiral center may be independently R, S, or any mixture of R and S. For example, in some embodiments, a chiral center may have an R:S ratio of between about 100:0 and about 50:50 ("racemate"), between about 100:0 and about 75:25, between about 100:0 and about 85:15, between about 100:0 and about 90:10, between about 100:0 and about 95:5, between about 100:0 and about 98:2, between about 100:0 and about 99:1, between about 0:100 and 50:50, between about 0:100 and about 25:75, between about 0:100 and about 15:85, between about 0:100 and about 10:90, between about 0:100 and about 5:95, between about 0:100 and about 2:98, between about 0:100 and about 1:99, between about 75:25 and 25:75, and about 50:50. Formulations of the disclosed compounds comprising a greater ratio of one or more isomers (i.e., R and/or 5) may possess enhanced therapeutic characteristic relative to racemic formulations of a disclosed compounds or mixture of compounds. In some instances, chemical formulas contain the descriptor "—(R)—" or "—(S)—" that is further attached to solid wedge or dashed wedge. This descriptor is intended to show a methine carbon (CH) that is attached to three other substituents and has either the indicated R or S configuration.

Disclosed compounds may provide for efficient cation channel opening at the NMDA receptor, e.g. may bind or associate with the glutamate site or glycine site or other modulatory site of the NMDA receptor to assist in opening the cation channel. The disclosed compounds may be used to regulate (turn on or turn off) the NMDA receptor through action as an agonist or antagonist.

The compounds described herein, in some embodiments, may bind to a specific NMDA receptor subtypes. For example, a disclosed compound may bind to one NMDA subtype and not another. In some embodiments, a disclosed compound may bind to one, or more than one NMDA subtype, and/or may have substantially less (or substantial no) binding activity to certain other NMDA subtypes.

The compounds as described herein may bind to NMDA receptors. A disclosed compound may bind to the NMDA receptor resulting in agonist-like activity (facilitation) over a certain dosing range and/or may bind to the NMDA receptor resulting in antagonist-like activity (inhibition) over a certain dosing range. In some embodiments, a disclosed compound may possess a potency that is 10-fold or greater than the activity of existing NMDA receptor modulators.

The disclosed compounds may exhibit a high therapeutic index. The therapeutic index, as used herein, refers to the ratio of the dose that produces a toxicity in 50% of the population (i.e., $TD_{50}$) to the minimum effective dose for 50% of the population (i.e., $ED_{50}$). Thus, the therapeutic index=$(TD_{50}):(ED_{50})$. In some embodiments, a disclosed compound may have a therapeutic index of at least about 10:1, at least about 50:1, at least about 100:1, at least about 200:1, at least about 500:1, or at least about 1000:1.

Compositions

In other aspects of the disclosure, a pharmaceutical formulation or a pharmaceutical composition including a disclosed compound and a pharmaceutically acceptable excipient is provided. In some embodiments, a pharmaceutical composition comprises a racemic mixture of one or more of the disclosed compounds.

A formulation can be prepared in any of a variety of forms for use such as for administering an active agent to a patient, who may be in need thereof, as are known in the pharmaceutical arts. For example, the pharmaceutical compositions of the present disclosure can be formulated for administration in solid or liquid form, including those adapted for the following: (1) oral administration, for example, drenches (aqueous or non-aqueous solutions or suspensions), tablets (e.g., those targeted for buccal, sublingual, and/or systemic absorption), boluses, powders, granules, and pastes for application to the tongue; (2) parenteral administration by, for example, subcutaneous, intramuscular, intraperitoneal, intravenous or epidural injection as, for example, a sterile solution or suspension, or sustained-release formulation; (3) topical administration, for example, as a cream, ointment, or a controlled-release patch or spray applied to the skin; (4) intravaginal or intrarectal administration, for example, as a pessary, cream or foam; (5) sublingual administration; (6) ocular administration; (7) transdermal administration; or (8) nasal administration.

For example, pharmaceutical compositions of the disclosure can be suitable for delivery to the eye, i.e., ocularly. Related methods can include administering a pharmaceutically effective amount of a disclosed compound or a pharmaceutical composition including a disclosed compound to a patient in need thereof, for example, to an eye of the patient, where administering can be topically, subconjunctively, subtenonly, intravitreally, retrobulbarly, peribulbarly, intracornerally, and/or systemically.

Amounts of a disclosed compound as described herein in a formulation may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier.

The specification for the dosage unit forms are dictated by and directly dependent on (a) the unique characteristics of the compound selected and the particular therapeutic effect to be achieved, and (b) the limitations inherent in the art of compounding such an active compound for the treatment of sensitivity in individuals.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin.

The compounds can be administered in a time release formulation, for example in a composition which includes a slow release polymer. The compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

Sterile injectable solutions can be prepared by incorporating the compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In some embodiments, a compound can be formulated with one or more additional compounds that enhance the solubility of the compound.

Methods

Methods of the disclosure for treating a condition in a patient in need thereof include administering a therapeutically effective amount of a compound described herein or a composition including such a compound. In some embodiments, the condition may be a mental condition. For example, a mental illness may be treated. In another aspect, a nervous system condition may be treated. For example, a condition that affects the central nervous system, the peripheral nervous system, and/or the eye may be treated. In some embodiments, neurodegenerative diseases may be treated.

In some embodiments, the methods include administering a compound to treat patients suffering from autism, anxiety, depression, bipolar disorder, attention deficit disorder, attention deficit hyperactivity disorder (ADHD), schizophrenia, a psychotic disorder, a psychotic symptom, social withdrawal, obsessive-compulsive disorder (OCD), phobia, post-traumatic stress syndrome, a behavior disorder, an impulse control disorder, a substance abuse disorder (e.g., a withdrawal symptom, opiate addiction, nicotine addiction, and ethanol addition), a sleep disorder, a memory disorder (e.g., a deficit, loss, or reduced ability to make new memories), a learning disorder, urinary incontinence, multiple system atrophy, progressive supra-nuclear palsy, Friedrich's ataxia, Down's syndrome, fragile X syndrome, tuberous sclerosis, olivio-ponto-cerebellar atrophy, cerebral palsy, drug-induced optic neuritis, ischemic retinopathy, diabetic retinopathy, glaucoma, dementia, AIDS dementia, Alzheimer's disease, Huntington's chorea, spasticity, myoclonus, muscle spasm, infantile spasm, Tourette's syndrome, epilepsy, cerebral ischemia, stroke, a brain tumor, traumatic brain injury, cardiac arrest, myelopathy, spinal cord injury, peripheral neuropathy, acute neuropathic pain, and chronic neuropathic pain.

In some embodiments, methods of treating a memory disorder associated with aging, schizophrenia, special learning disorders, seizures, post-stroke convulsions, brain ischemia, hypoglycemia, cardiac arrest, epilepsy, Lewy body dementia, migraine, AIDS dementia, Huntington's chorea, Parkinson's disease, early stage Alzheimer's disease, and Alzheimer's disease are provided.

In certain embodiments, methods for treating schizophrenia are provided. For example, paranoid type schizophrenia, disorganized type schizophrenia (i.e., hebephrenic schizophrenia), catatonic type schizophrenia, undifferentiated type schizophrenia, residual type schizophrenia, post-schizophrenic depression, and simple schizophrenia may be treated using the methods and compositions disclosed herein. Psychotic disorders such as schizoaffective disorders, delusional disorders, brief psychotic disorders, shared psychotic disorders, and psychotic disorders with delusions or hallucinations may also be treated using the compositions disclosed herein.

Paranoid schizophrenia may be characterized where delusions or auditory hallucinations are present, but thought disorder, disorganized behavior, or affective flattening are not. Delusions may be persecutory and/or grandiose, but in addition to these, other themes such as jealousy, religiosity, or somatization may also be present. Disorganized type schizophrenia may be characterized where thought disorder and flat affect are present together. Catatonic type schizophrenia may be characterized where the patient may be almost immobile or exhibit agitated, purposeless movement. Symptoms can include catatonic stupor and waxy flexibility. Undifferentiated type schizophrenia may be characterized where psychotic symptoms are present but the criteria for paranoid, disorganized, or catatonic types have not been met. Residual type schizophrenia may be characterized where positive symptoms are present at a low intensity only. Post-schizophrenic depression may be characterized where a depressive episode arises in the aftermath of a schizophrenic illness where some low-level schizophrenic symptoms may still be present. Simple schizophrenia may be characterized by insidious and progressive development of prominent negative symptoms with no history of psychotic episodes.

In some embodiments, methods are provided for treating psychotic symptoms that may be present in other mental disorders, including, but not limited to, bipolar disorder, borderline personality disorder, drug intoxication, and drug-induced psychosis. In some embodiments, methods for treating delusions (e.g., "non-bizarre") that may be present in, for example, delusional disorder are provided.

In various embodiments, methods for treating social withdrawal in conditions including, but not limited to, social anxiety disorder, avoidant personality disorder, and schizotypal personality disorder are provided.

In some embodiments, the disclosure provides methods for treating a neurodevelopmental disorder related to synaptic dysfunction in a patient in need thereof, where the methods generally include administering to the patient a therapeutically effective amount of a disclosed compound, or a pharmaceutical composition including a disclosed compound. In certain embodiments, the neurodevelopmental disorder related to synaptic dysfunction can be Rett syndrome also known as cerebroatrophic hyperammonemia, MECP2 duplication syndrome (e.g., a MECP2 disorder), CDKL5 syndrome, fragile X syndrome (e.g., a FMR1 disorder), tuberous sclerosis (e.g., a TSC1 disorder and/or a TSC2 disorder), neurofibromatosis (e.g., a NF1 disorder), Angelman syndrome (e.g., a UBE3A disorder), the PTEN hamartoma tumor syndrome, Phelan-McDermid syndrome (e.g., a SHANK3 disorder), or infantile spasms. In particular embodiments, the neurodevelopmental disorder can be caused by mutations in the neuroligin (e.g., a NLGN3 disorder and/or a NLGN2 disorder) and/or the neurexin (e.g., a NRXN1 disorder).

In some embodiments, methods are provided for treating neuropathic pain. The neuropathic pain may be acute or chronic. In some cases, the neuropathic pain may be associated with a condition such as herpes, HIV, traumatic nerve injury, stroke, post-ischemia, chronic back pain, post-herpetic neuralgia, fibromyalgia, reflex sympathetic dystrophy, complex regional pain syndrome, spinal cord injury, sciatica, phantom limb pain, diabetic neuropathy such as diabetic peripheral neuropathy ("DPN"), and cancer chemotherapeutic-induced neuropathic pain. Methods for enhancing pain relief and for providing analgesia to a patient are also provided.

Further methods include a method of treating autism and/or an autism spectrum disorder in a patient need thereof, comprising administering an effective amount of a compound to the patient. In certain embodiments, a method for reducing the symptoms of autism in a patient in need thereof comprises administering an effective amount of a disclosed compound to the patient. For example, upon administration, the compound may decrease the incidence of one or more symptoms of autism such as eye contact avoidance, failure to socialize, attention deficit, poor mood, hyperactivity, abnormal sound sensitivity, inappropriate speech, disrupted sleep, and perseveration. Such decreased incidence may be measured relative to the incidence in the untreated individual or an untreated individual(s).

Also provided herein is a method of modulating an autism target gene expression in a cell comprising contacting a cell with an effective amount of a compound described herein. The autism gene expression may be for example, selected from ABAT, APOE, CHRNA4, GABRA5, GFAP, GRIN2A, PDYN, and PENK. In some embodiments, a method of modulating synaptic plasticity in a patient suffering from a synaptic plasticity related disorder is provided, comprising administering to the patient an effective amount of a compound.

In some embodiments, a method of treating Alzheimer's disease, or e.g., treatment of memory loss that e.g., accompanies early stage Alzheimer's disease, in a patient in need thereof is provided, comprising administering a compound. Also provided herein is a method of modulating an Alzheimer's amyloid protein (e.g., beta amyloid peptide, e.g. the isoform $A\beta_{1-42}$), in-vitro or in-vivo (e.g. in a cell) comprising contacting the protein with an effective amount of a compound is disclosed. For example, in some embodiments, a compound may block the ability of such amyloid protein to inhibit long-term potentiation in hippocampal slices as well as apoptotic neuronal cell death. In some embodiments, a disclosed compound may provide neuroprotective properties to a Alzheimer's patient in need thereof, for example, may provide a therapeutic effect on later stage Alzheimer's-associated neuronal cell death.

In certain embodiments, the disclosed methods include treating a psychosis or a pseudobulbar affect ("PBA") that is induced by another condition such as a stroke, amyotrophic lateral sclerosis (ALS or Lou Gehrig's disease), multiple sclerosis, traumatic brain injury, Alzheimer's disease, dementia, and/or Parkinson's disease. Such methods, as with other methods of the disclosure, include administration of a pharmaceutically effective amount of a disclosed compound to a patient in need thereof.

In some embodiments, a method of treating depression includes administering a therapeutically effective amount of a compound described herein. In some embodiments, the treatment may relieve depression or a symptom of depression without affecting behavior or motor coordination and without inducing or promoting seizure activity. Exemplary depression conditions that are expected to be treated according to this aspect include, but are not limited to, major depressive disorder, dysthymic disorder, psychotic depression, postpartum depression, premenstrual syndrome, premenstrual dysphoric disorder, seasonal affective disorder (SAD), bipolar disorder (or manic depressive disorder), mood disorder, and depressions caused by chronic medical conditions such as cancer or chronic pain, chemotherapy, chronic stress, and post traumatic stress disorders. In addition, patients suffering from any form of depression often experience anxiety. Various symptoms associated with anxiety include fear, panic, heart palpitations, shortness of breath, fatigue, nausea, and headaches among others. Anxiety or any of the symptoms thereof may be treated by administering a compound as described herein.

Also provided herein are methods of treating a condition in treatment-resistant patients, e.g., patients suffering from a mental or central nervous system condition that does not, and/or has not, responded to adequate courses of at least one, or at least two, other compounds or therapeutics. For example, provided herein is a method of treating depression in a treatment resistant patient, comprising a) optionally identifying the patient as treatment resistant and b) administering an effective dose of a compound to said patient.

In some embodiments, a compound described herein may be used for acute care of a patient. For example, a compound may be administered to a patient to treat a particular episode (e.g., a severe episode) of a condition disclosed herein.

Also provided herein are combination therapies comprising a compound of the disclosure in combination with one or more other active agents. For example, a compound may be combined with one or more antidepressants, such as tricyclic antidepressants, MAO-I's, SSRI's, and double and triple uptake inhibitors and/or anxiolytic drugs. Exemplary drugs that may be used in combination with a compound include Anafranil, Adapin, Aventyl, Elavil, Norpramin, Pamelor, Pertofrane, Sinequan, Surmontil, Tofranil, Vivactil, Parnate, Nardil, Marplan, Celexa, Lexapro, Luvox, Paxil, Prozac, Zoloft, Wellbutrin, Effexor, Remeron, Cymbalta, Desyrel (trazodone), and Ludiomill. In another example, a compound may be combined with an antipsychotic medication. Non-limiting examples of antipsychotics include butyrophenones, phenothiazines, thioxanthenes, clozapine, olanzapine, risperidone, quetiapine, ziprasidone, amisulpride, asenapine, paliperidone, iloperidone, zotepine, sertindole, lurasidone, and aripiprazole. It should be understood that combinations of a compound and one or more of the above therapeutics may be used for treatment of any suitable condition and are not limited to use as antidepressants or antipsychotics.

EXAMPLES

The following examples are provided for illustrative purposes only, and are not intended to limit the scope of the disclosure.

The following abbreviations may be used herein and have the indicated definitions: Ac is acetyl (—C(O)CH$_3$), AIDS is acquired immune deficiency syndrome, Boc and BOC are tert-butoxycarbonyl, Boc$_2$O is di-tert-butyl dicarbonate, Bn is benzyl, DCM is dichloromethane, DIPEA is N,N-diisopropylethylamine, DMAP is 4-dimethylaminopyridine, DMSO is dimethyl sulfoxide, ESI is electrospray ionization, EtOAc is ethyl acetate, h is hour, HIV is human immunodeficiency virus, HPLC is high performance liquid chromatography, LCMS is liquid chromatography/mass spectrometry, LiHMDS is lithium hexamethyldisilazane, NMDAR is N-methyl-d-apartate receptor, NMR is nuclear magnetic resonance, RT is room temperature (e.g., from about 20° C. to about 25° C.), TLC is thin layer chromatography, TFA is trifluoroacetic acid, and THF is tetrahydrofuran.

Example 1: Synthesis of Exemplary Compounds

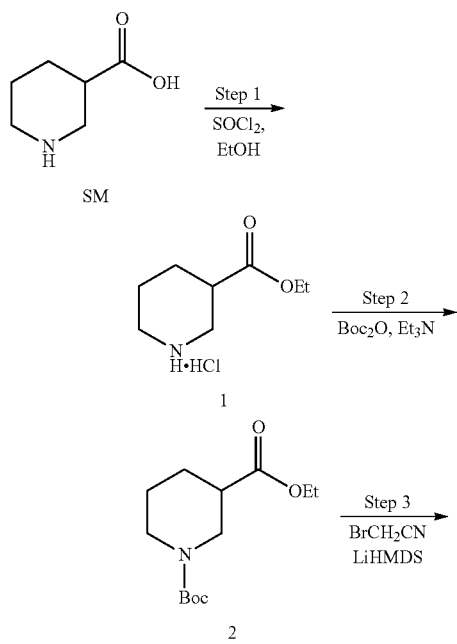

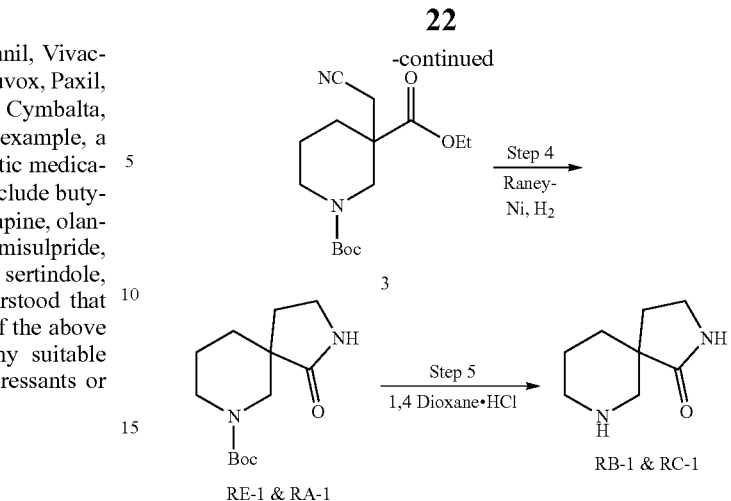

Synthesis of ethyl piperidine-3-carboxylate Hydrochloride (1)

To a stirring solution of piperidine-3-carboxylic acid (SM) (20 g, 154.8 mmol) in EtOH was added thionyl chloride (45 ml, 619.2 mmol) at 0° C. and heated to reflux for 24 h. The reaction mixture was warmed to RT and concentrated under reduced pressure. Crude material was triturated with diethyl ether and dried to afford compound 1.HCl salt (29 g, 99%) as thick syrup.

$^1$H-NMR: (400 MHz, DMSO-d$_6$): δ 9.40 (s, 1H), 9.25 (s, 1H), 4.09 (q, J=7.2 Hz, 2H), 3.32.3.13 (m, 2H), 2.94-2.75 (m, 3H), 1.99-1.96 (m, 1H), 1.77-1.71 (m, 2H), 1.60-1.58 (1H), 1.16 (t, J=7.2 Hz, 3H).

LCMS (ESI): m/z 157.3 [M$^+$]

Synthesis of 1-(tert-butyl) 3-ethyl piperidine-1,3-dicarboxylate (2)

To a solution of compound 1.HCl salt (30 g, 154.9 mmol) in CH$_2$Cl$_2$ (600 mL) was added Et$_3$N (65 mL, 464.7 mmol) at 0° C. and stirred for 10 min. Then Boc-anhydride (40 mL, 185.8 mmol) at 0° C. warmed to RT and stirred for 16 h. After consumption of the starting material (by TLC), the reaction was diluted with DCM (200 mL) and washed with water (3×200 mL). Organic layer was dried over Na$_2$SO$_4$ and concentrated under reduced pressure to afford crude compound which was purified by column chromatography by eluting with 20% EtOAc/hexanes to obtain compound 2 (34 g, 85%) as thick syrup.

$^1$H-NMR: (400 MHz, DMSO-d$_6$): δ 4.06 (q, J=7.2 Hz, 2H), 3.89.3.85 (m, 1H), 3.64.3.59 (m, 1H), 2.93-2.88 (m, 2H), 2.42.2.37 (m, 1H), 1.89-1.86 (m, 1H), 1.63-1.54 (m, 2H), 1.38 (s, 9H), 1.37-1.34 (m, 1H), 1.18 (t, J=7.2 Hz, 3H).

LCMS (ESI): m/z 156.1 [(M$^+$+1)-Boc]

Synthesis of 1-(tert-butyl) 3-ethyl 3-(cyanomethyl) piperidine-1,3-dicarboxylate (3)

To a stirring solution of compound 2 (15 g, 58.3 mmol) in THF (120 mL) was added LiHMDS (1M in THF) (116 mL, 116.7 mmol) drop wise at −40° C. and stirred for 15 minutes. Then bromo acetonitrile (8.4 g, 70.1 mmol) was added drop wise at −40° C. and stirred for 5 h. After consumption of the starting material (by TLC), the reaction was quenched with aqueous NH$_4$Cl solution (100 mL) and extracted with EtOAc (2×200 mL). The combined organic layer was washed with water (2×150 mL) followed by brine solution (2×100 mL). The organic layer was dried over $Na_2SO_4$ and concentrated to obtain crude compound which was purified by column chromatography by eluting 30% EtOAc/hexanes to afford compound 3 (3 g, 17%) as thick syrup.

$^1$H NMR (400 MHz, DMSO-$d_6$): δ 4.16 (q, J=7.2 Hz, 2H), 3.78-3.72 (m, 1H), 3.56-3.52 (m, 1H), 3.23-3.12 (m, 2H), 2.77-2.68 (m, 2H), 2.01-1.94 (m, 1H), 1.68-1.58 (m, 3H), 1.39 (s, 9H), 1.24 (t, J=7.1 Hz, 3H).

LCMS (ESI): m/z 197.3 [(M$^+$+1)-Boc]

Synthesis of tert-butyl 1-oxo-2,7-diazaspiro[4.5] decane-7-carboxylate (4)

To a stirring solution of compound 3 (2 g, 6.75 mmol) in ethanol (20 mL) was added Raney nickel (2 g) at RT under nitrogen atmosphere and then allowed to stir for 16 h under $H_2$ atmosphere. Then methanolic ammonia (4 mL) was added to the reaction mixture and continued stirring for 16 h under $H_2$ atmosphere (balloon pressure). After completion of the reaction by TLC, the reaction mixture was filtered through a pad of celite and the filtrate was concentrated under reduced pressure. Crude material was purified by combiflash column chromatography by eluting with 50% EtOAc/hexanes to afford to afford racemic compound 4 (750 mg) followed by chiral HPLC purification to obtain RE-1 (300 mg, %) and RA-1 (310 mg, %) as off white solids.

RE-1
$^1$H NMR (400 MHz, DMSO-$d_6$): δ 7.64 (s, 1H), 3.97-3.82 (m, 1H), 3.66 (br d, J=1.5 Hz, 1H), 3.15 (br t, J=7.0 Hz, 2H), 2.86-2.61 (m, 2H), 1.97-1.86 (m, 1H), 1.84-1.74 (m, 1H), 1.70-1.53 (m, 2H), 1.46 (br d, J=14.4 Hz, 1H), 1.39 (s, 10H).

LCMS (ESI): m/z 255.3 [M$^+$+1]
HPLC: 99.45%
Chiral HPLC: 100.00%

RA-1
$^1$H NMR (400 MHz, DMSO-$d_6$): δ 7.64 (s, 1H), 3.89 (br d, J=7.7 Hz, 1H), 3.66 (br s, 1H), 3.15 (br t, J=7.0 Hz, 2H), 2.84-2.63 (m, 2H), 1.96-1.87 (m, 1H), 1.84-1.74 (m, 1H), 1.70-1.54 (m, 2H), 1.49-1.44 (m, 2H), 1.39 (s, 9H).

LCMS (ESI): m/z 255.3 [M$^+$+1]
HPLC: 99.55%
Chiral HPLC: 100.00%

Synthesis of 2,7-diazaspiro[4.5]decan-1-one (RB-1.HCl)

To a stirring solution of RE-1 (201 mg, 0.79 mmol) in $CH_2Cl_2$ (5 mL) was added 2 M HCl-1, 4-Dioxane (4 mL) at 0° C. warmed to RT and stirred for 2 h, the reaction mixture was concentrated under reduced pressure to afford crude compound which was triturated with ether and n-pentane (2×20 mL) and dried to obtain RB-1.HCl (148 g, 99%) as off white solid.

$^1$H NMR (400 MHz, DMSO-$d_6$): δ 8.69 (br s, 2H), 7.92 (s, 1H), 3.25-3.15 (m, 2H), 3.08-2.91 (m, 4H), 2.13-2.09 (m, 1H), 1.98-1.88 (m, 1H), 1.86-1.76 (m, 1H), 1.74-1.63 (m, 2H), 1.59-1.50 (m, 1H).

LCMS (ESI): m/z 155.0 [M++1]
HPLC: 99.55%
Chiral HPLC: 100.00%

Synthesis of 2,7-diazaspiro[4.5]decan-1-one (RC-1.HCl)

To a stirring solution of RA-1 (218 mg, 0.85 mmol) in $CH_2Cl_2$ (5 mL) was added 2 M HCl-1,4-Dioxane (4 mL) at 0° C., warmed to RT and stirred for 2 h. the reaction mixture was concentrated under reduced pressure to afford crude compound which was triturated with ether and n-pentane (2×20 mL) and dried to obtain RC-1.HCl (150 g, 92%) as off white solid.

$^1$H NMR (400 MHz, DMSO-$d_6$): δ 8.85 (br s, 2H), 7.91 (s, 1H), 3.24-3.16 (m, 2H), 3.10-2.88 (m, 4H), 2.16-2.12 (m, 1H), 1.98-1.90 (m, 1H), 1.86-1.75 (m, 1H), 1.75-1.63 (m, 2H), 1.57-1.52 (m, 1H).

LCMS (ESI): m/z 155.0 [M$^+$+1]
HPLC: 99.65%
Chiral HPLC: 100.00%

Example 2

Following the above procedures, the following compounds were or are prepared. It should be appreciated that the compound in the first column is a different stereoisomer, for example, a different enantiomer and/or different diastereomer, from the compound in the second column

| Structure | Compound |
|---|---|
| 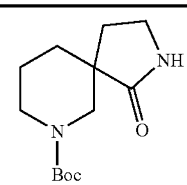 | RE-1 |
| 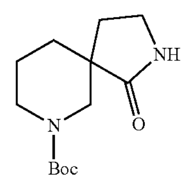 [SMILES: CC(C)(C)OC(=O)N1CCCC2(CCNC2=O)C1] | RA-1 |
| 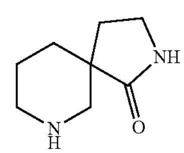 [SMILES: O=C1NCCC12CCCNC2] | RB-1 |
| 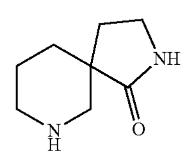 [SMILES: O=C1NCCC12CCCNC2] | RC-1 |
| 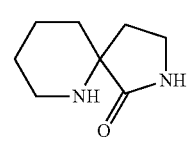 [SMILES: O=C1NCCC12CCCCN2] | RG-601 |
| 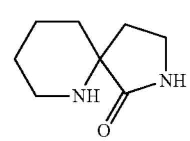 [SMILES: O=C1NCCC12CCCCN2] | RG-602 |
| 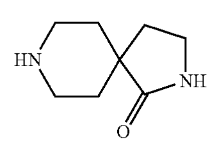 | RG-603 |

| Structure | Compound |
|---|---|
| 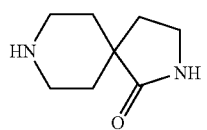 | RG-604 |
| 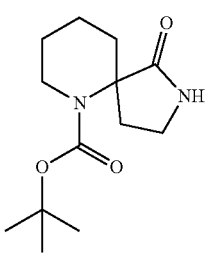 [SMILES: CC(C)(C)OC(=O)N1CCCCC12CCNC2=O] | RG-605 |
| 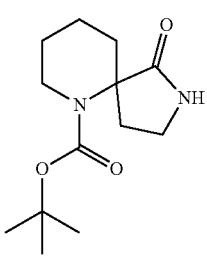 [SMILES: CC(C)(C)OC(=O)N1CCCCC12CCNC2=O] | RG-606 |
| 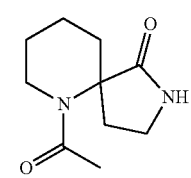 | RG-607 |
| 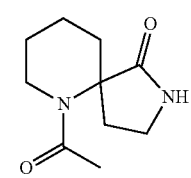 | RG-608 |
| 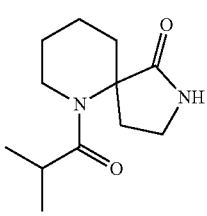 [SMILES: CC(C)C(=O)N1CCCCC12CCNC2=O] | RG-609 |
| 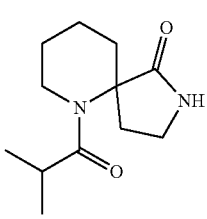 [SMILES: CC(C)C(=O)N1CCCCC12CCNC2=O] | RG-610 |
| Structure | Compound |
|---|---|
| 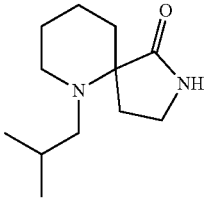 | RG-611 |
| 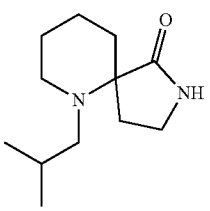 | RG-612 |
| 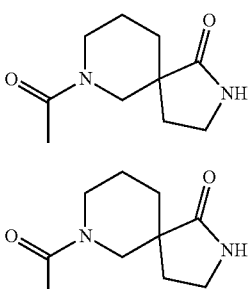 | RG-613 |
| 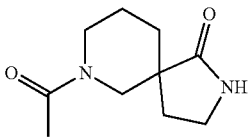 | RG-614 |
| 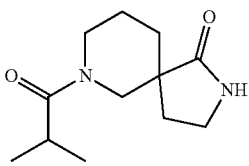 [SMILES: CC(C)C(=O)N1CCCC2(CCNC2=O)C1] | RG-615 |
| 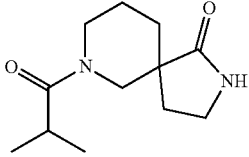 [SMILES: CC(C)C(=O)N1CCCC2(CCNC2=O)C1] | RG-616 |
| 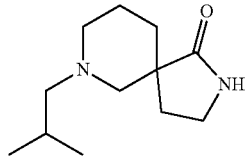 | RG-617 |
| 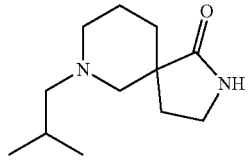 | RG-618 |
| 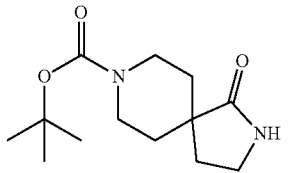 [SMILES: CC(C)(C)OC(=O)N1CCC2(CCNC2=O)CC1] | RG-619 |

| Structure | Compound |
|---|---|
| 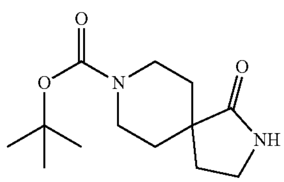 [SMILES: CC(C)(C)OC(=O)N1CCC2(CCNC2=O)CC1] | RG-620 |
| 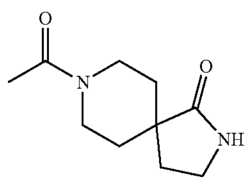 | RG-621 |
| 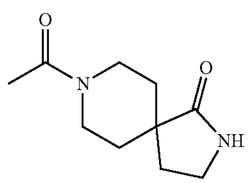 | RG-622 |
| 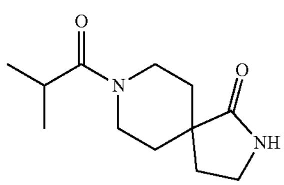 [SMILES: CC(C)C(=O)N1CCC2(CCNC2=O)CC1] | RG-623 |
| 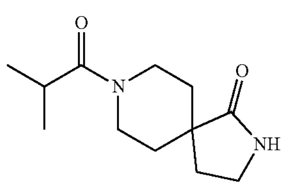 [SMILES: CC(C)C(=O)N1CCC2(CCNC2=O)CC1] | RG-624 |
| 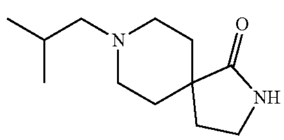 | RG-625 |
| 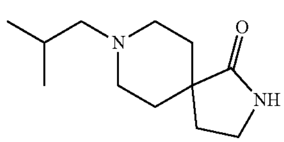 | RG-626 |
| 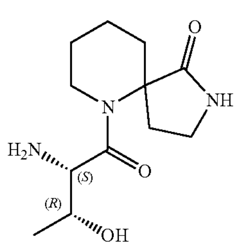 | RG-627 |
| | RG-628 |
| | RG-629 |
| | RG-630 |
| | RG-631 |
| | RG-632 |
| | RG-633 |

| Structure | Compound |
|---|---|
| 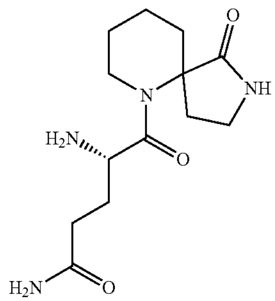 [SMILES: NC(=O)CC[C@H](N)C(=O)N1CCCCC12CCNC2=O] | RG-634 |
| 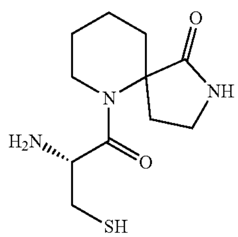 [SMILES: N[C@@H](CS)C(=O)N1CCCCC12CCNC2=O] | RG-635 |
| 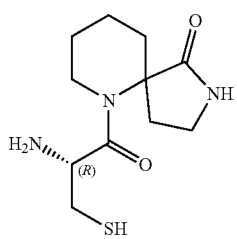 | RG-636 |
| 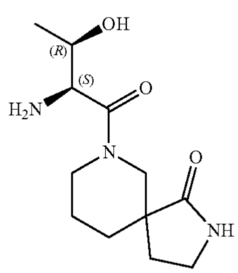 | RG-637 |
| 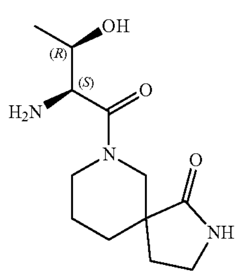 | RG-638 |
| 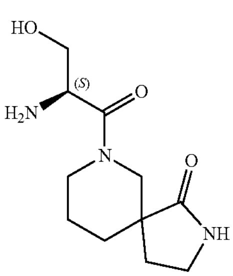 | RG-639 |
| | RG-640 |
| | RG-641 |
| | RG-642 |
| | RG-643 |
| | RG-644 |
| | RG-645 |

-continued

| Structure | Compound |
|---|---|
| (chemical structure) | RG-646 |
| (chemical structure) | RG-647 |
| (chemical structure) | RG-648 |
| (chemical structure) | RG-649 |
| (chemical structure) | RG-650 |
| (chemical structure) | RG-651 |
| (chemical structure) | RG-652 |
| (chemical structure) | RG-653 |

-continued

| Structure | Compound |
|---|---|
| (chemical structure) | RG-654 |
| (chemical structure) | RG-655 |
| (chemical structure) | RG-656 |
| (chemical structure) | RG-657 |
| (chemical structure) | RG-658 |
| (chemical structure) | RG-659 |
| (chemical structure) | RG-660 |
| (chemical structure) | RG-661 |

| Structure | Compound |
|---|---|
| 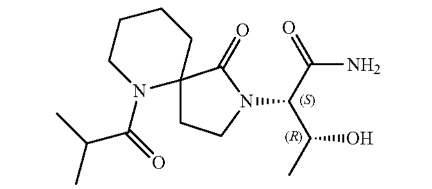 | RG-662 |
| 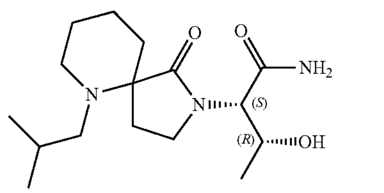 | RG-663 |
| 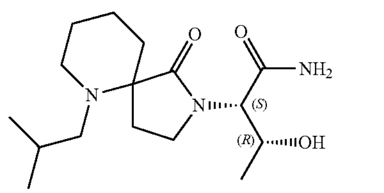 | RG-664 |
| 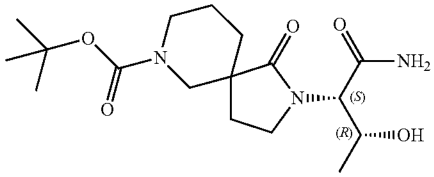 | RG-665 |
| 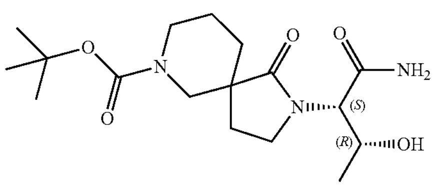 | RG-666 |
| 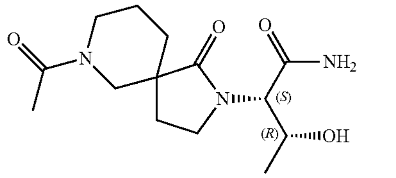 | RG-667 |
| 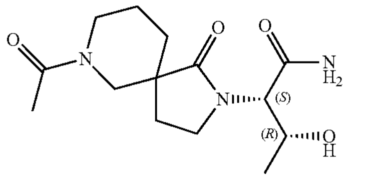 | RG-668 |
| 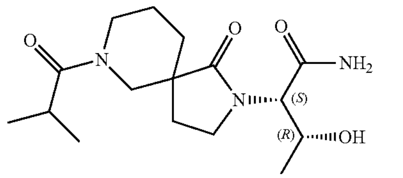 | RG-669 |
| | RG-670 |
| | RG-671 |
| | RG-672 |
| | RG-673 |
| | RG-674 |
| | RG-675 |
| | RG-676 |

35

-continued

| Structure | Compound |
|---|---|
| 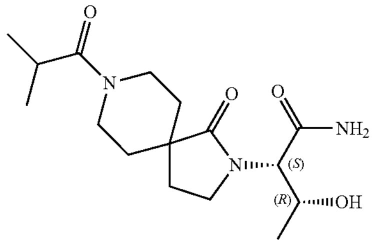 | RG-677 |
| 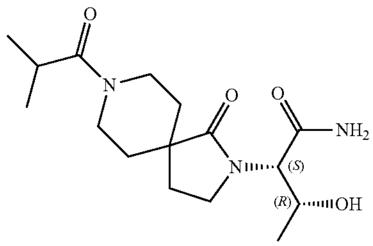 | RG-678 |
| 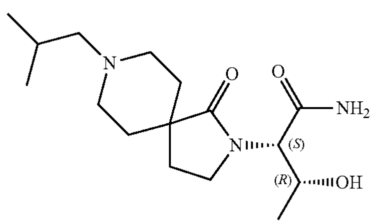 | RG-679 |
| 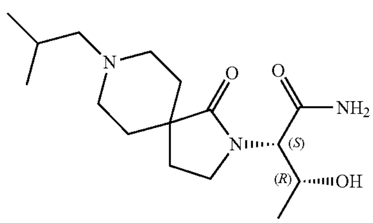 | RG-680 |

Example 3: Synthesis of Exemplary Compounds

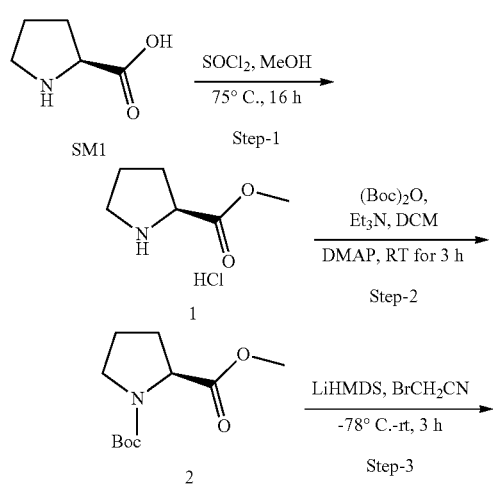

36

-continued

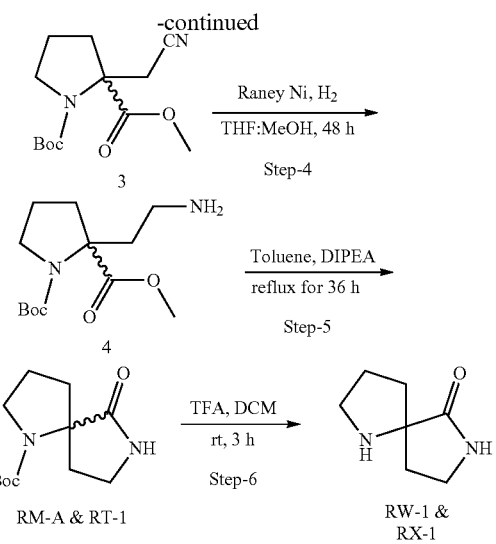

Synthesis of methyl L-prolinate (1)

To a stirred solution of L-proline SM 1(100.0 g, 869 mmol) in MeOH (1 L), thionyl chloride (100 mL) was added at 0° C. heated to 75° C. and stirred for 16 h. After consumption of the starting material (by TLC), the reaction mixture was concentrated under reduced pressure to afford compound 1 (140 g, crude) as thick oil (HCl salt). Crude compound was use as such for next step without purification.

$^1$H NMR (400 MHz, DMSO-$d_6$) δ 10.50 (br s, 1H), 9.13 (br s, 1H), 4.35 (m, 1H), 3.75 (s, 3H), 3.26-3.11 (m, 2H), 2.28-2.20 (m, 1H), 2.05-1.83 (m, 3H).

Synthesis of 1-(tert-butyl) 2-methyl (S)-pyrrolidine-1,2-dicarboxylate (2)

To a stirred solution of compound 1 (140.0 g, 0.848 mol) in CH$_2$Cl$_2$ (1.4 L), triethylamine (295 mL, 2.12 mmol) was added at 0° C. and stirred for 15 min. Boc anhydride (240 g, 1.10 mmol) was added drop wise at 0° C. over a period of 30 min followed by addition of DMAP (20.7 g, 0.169 mmol). The reaction mixture was warmed to RT and stirred for 3 h. After consumption of the starting material (by TLC), the reaction mixture was quenched with ice-cold water (500 mL) and extracted with CH$_2$Cl$_2$ (3×300 mL). Combined organic layer was washed with brine (150 mL), dried over Na$_2$SO$_4$ and concentrated under reduced pressure to afford crude compound. The crude compound was purified by column chromatography with 20-30% EtOAc/hexanes to obtain compound 2 (190.0 g, 98%) as thick oil.

$^1$H NMR (400 MHz, DMSO-$d_6$) δ 4.18-413 (m, 1H), 3.63 (m, 3H), 3.41-3.24 (m, 2H), 2.28-2.11 (m, 1H), 1.90-1.73 (m, 3H), 1.32 (m, 9H).

Synthesis of 1-(tert-butyl) 2-methyl 2-(cyanomethyl)pyrrolidine-1,2-dicarboxylate (3)

To a stirred solution of compound 2 (20.0 g, 93.4 mmol) in THF (150 mL), LiHMDS (140 mL, 140 mmol) was added at −78° C. and stirred for 30 min. Bromoacetonitrile (12.3 mL, 102 mmol) was added at −78° C.; warmed to RT and stirred for 4 h. After consumption of the starting material (by TLC), the reaction mixture was quenched with saturated NH$_4$Cl solution (300 mL) and extracted with EtOAc (3×300 mL). Combined organic layer was washed with brine (100 mL), dried over $Na_2SO_4$ and concentrated under reduced pressure to give crude product. Obtained crude compound was purified by column chromatography using 40% EtOAc/hexane to provide enantiomeric mixture of compound 3 (15 g, 63%) as thick oil.

$^1$H NMR (400 MHz, DMSO-$d_6$) δ 3.64 (m, 3H), 3.57-3.46 (m, 1H), 3.42-3.36 (m, 1H), 3.26-3.09 (m, 5H), 2.25-2.16 (m, 2H), 2.04-1.83 (m, 2H), 1.37 (m, 9H).

Synthesis of 1-(tert-butyl) 2-methyl 2-(2-aminoethyl)pyrrolidine-1,2-dicarboxylate (4)

To a stirred solution of compound 3 (5.0 g, 18.6 mmol) in THF: MeOH (1:1, 200 mL), Raney nickel (4.0 g) was added at room temperature and stirred for 48 h at 50° C. under $H_2$ atmosphere. After consumption of the starting material (by TLC), the reaction mixture was filtered through a pad of celite and the pad was washed with MeOH (50 mL). The crude compound was purified by column chromatography using 5% MeOH/$CH_2Cl_2$ to provide enantiomeric mixture of compound 4 (2.5 g, 50%) as thick oil.

Synthesis of tert-butyl 6-oxo-1,7-diazaspiro[4.4]nonane-1-carboxylate (RM-1 & RT-1)

To a stirred solution of compound 4 (10.0 g, 36.9 mmol) in toluene (100 mL), DIPEA (7.7 mL, 44.2 mmol) was added and reaction mixture was heated to reflux for 36 h. After consumption of the starting material (by TLC), reaction mixture was evaporated under reduced pressure. Crude material was purified by Prep HPLC to obtain two separated isomers of compound RM-1 & RT-1 as thick oil.

Analytical data for RM-1:
$^1$H NMR (400 MHz, DMSO-$d_6$) δ 7.70 (m, 1H), 3.40-3.30 (m, 1H), 3.25-3.09 (m, 3H), 2.35-2.30 (m, 1H), 1.98-1.72 (m, 5H), 1.42 (s, 9H).
LCMS (ESI): m/z 263 [M$^+$+Na]
HPLC: 95.4%
Chiral HPLC: 100%

Analytical data for RT-1:
$^1$H NMR (400 MHz, DMSO-$d_6$) δ 7.70 (s, 1H), 3.40-3.30 (m, 1H), 3.25-3.09 (m, 3H), 2.35-2.30 (m, 1H), 1.98-1.70 (m, 5H), 1.45 (s, 9H).
LCMS (ESI): m/z 263 [M$^+$+Na]
HPLC: 97.1%
Chiral HPLC: 100%

Synthesis of 1,7-diazaspiro[4.4]nonan-6-one (RW-1 & RX-1)

To a stirred solution of compound 5 (1.5 g, 6.07 mmol) in $CH_2Cl_2$ (7 mL), trifluoroacetic (7 mL) was added and stirred at room temperature for 3 h. After consumption of the starting material (by TLC), the reaction mixture was concentrated under reduced pressure to obtain compound as a TFA salt. Obtained salt was dissolved in THF (5 ml), triethylamine (5 mL) was added and then stirred at room temperature for 5 h. The crude compound was purified by Prep HPLC to afford two separated isomers of compound RW-1 & RX-1 (free base) as thick oil.

Analytical data for RW-1:
$^1$H NMR (400 MHz, DMSO-$d_6$) δ 7.67 (s, 1H), 3.20-3.03 (m, 2H), 3.01-2.97 (m, 1H), 2.78-2.65 (m, 1H), 2.20-2.14 (brs, 1H), 1.99-1.80 (m, 2H), 1.78-1.60 (m, 4H).
LCMS (ESI): m/z 141.2 [M$^+$+1]
HPLC: 97.9%
Chiral HPLC: 100%

Analytical data for RX-1:
$^1$H NMR (400 MHz, DMSO-$d_6$) δ 7.67 (s, 1H), 3.19-3.02 (m, 2H), 3.01-2.97 (m, 1H), 2.78-2.70 (m, 1H), 1.98-1.80 (m, 2H), 1.78-1.60 (m, 4H).
LCMS (ESI): m/z 141.3 [M$^+$+1]
HPLC: 99.4%
Chiral HPLC: 99.0%

Example 4

Following the above procedures, the following compounds were or are prepared. It should be appreciated that the compound in the first column is a different stereoisomer, for example, a different enantiomer and/or different diastereomer, from the compound in the second column.

| Structure | Compound |
|---|---|
| 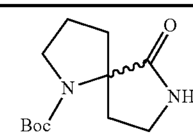 | RM-1 |
| 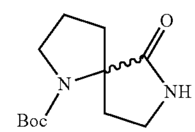 | RT-1 |
| 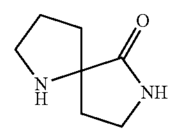 | RW-1 |
| 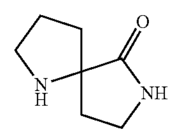 | RX-1 |
| 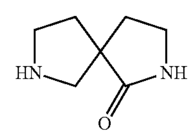 | RZ-401 |
| 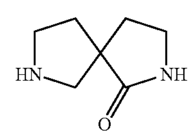 | RZ-402 |
| 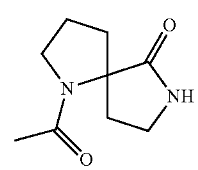 | RZ-403 |
| 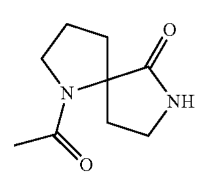 | RZ-404 |

| Structure | Compound |
|---|---|
| 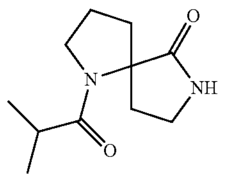 | RZ-405 |
| 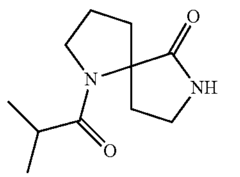 | RZ-406 |
| 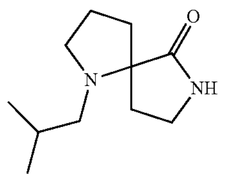 | RZ-407 |
| 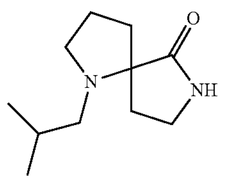 | RZ-408 |
| 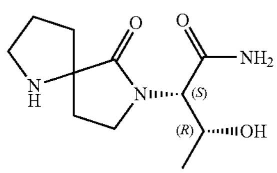 | RZ-409 |
| 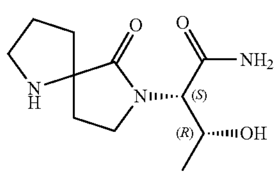 | RZ-410 |
| 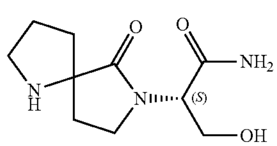 | RZ-411 |
| 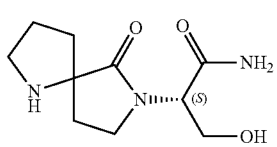 | RZ-412 |
| 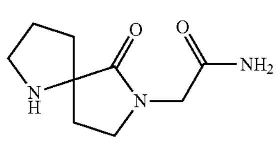 [SMILES: NC(=O)CN1CCC2(CCCN2)C1=O] | RZ-413 |
| | RZ-414 |
| | RZ-415 |
| | RZ-416 |
| | RZ-417 |
| | RZ-418 |
| | RZ-419 |
| | RZ-420 |

| Structure | Compound |
|---|---|
| 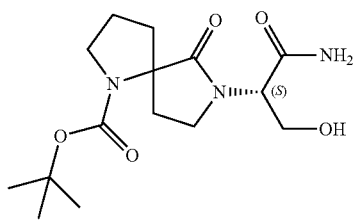 | RZ-421 |
| 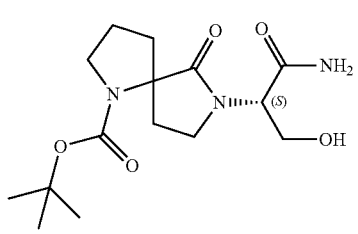 | RZ-422 |
| 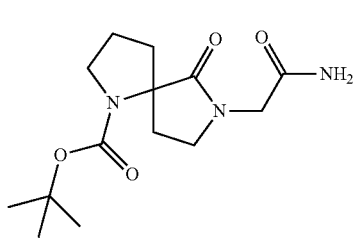 [SMILES: CC(C)(C)OC(=O)N1CCCC12CCN(CC(N)=O)C2=O] | RZ-423 |
| 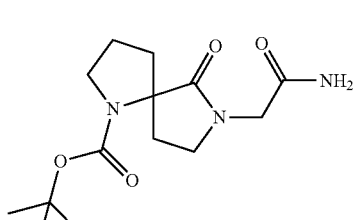 | RZ-424 |
| 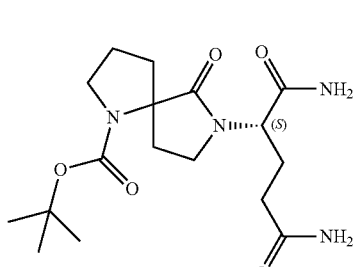 | RZ-425 |
| 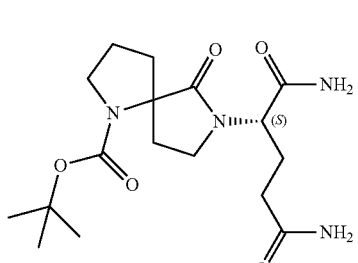 | RZ-426 |
| Structure | Compound |
|---|---|
| 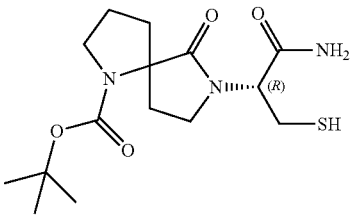 | RZ-427 |
| 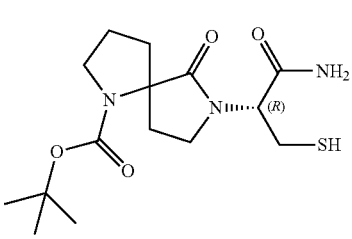 | RZ-428 |
| 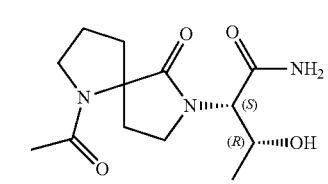 | RZ-429 |
| 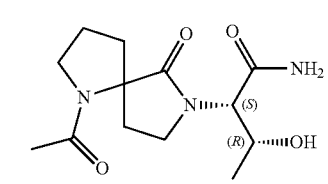 | RZ-430 |
| 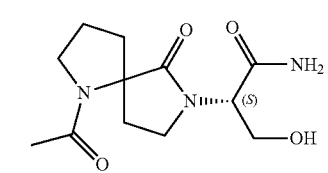 | RZ-431 |
| 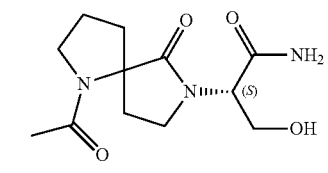 | RZ-432 |
| 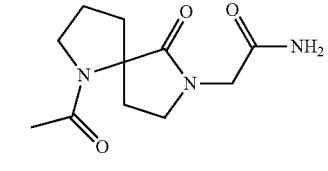 [SMILES: CC(=O)N1CCCC12CCN(CC(N)=O)C2=O] | RZ-433 |
| 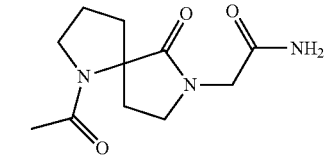 | RZ-434 |

| Structure | Compound |
|---|---|
| 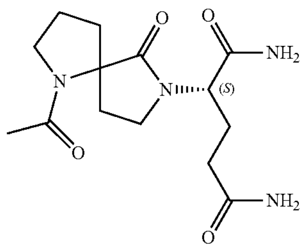 | RZ-435 |
| 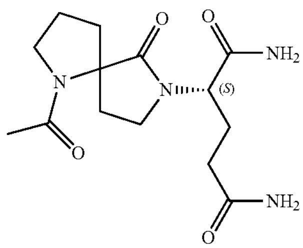 | RZ-436 |
| 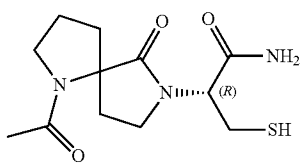 | RZ-437 |
| 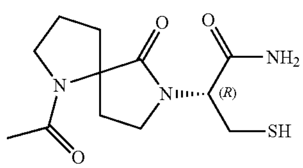 | RZ-438 |
| 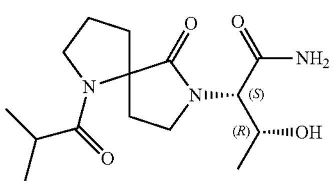 | RZ-439 |
| 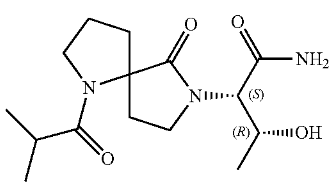 | RZ-440 |
| 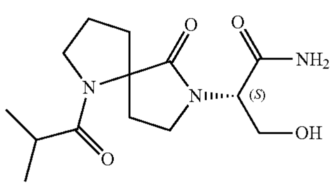 | RZ-441 |
| 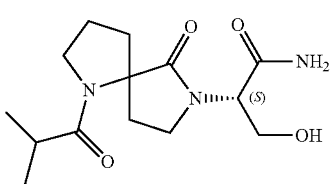 | RZ-442 |
| | RZ-443 |
| | RZ-444 |
| | RZ-445 |
| | RZ-446 |
| | RZ-447 |
| | RZ-448 |
| | RZ-449 |

| Structure | Compound |
|---|---|
| 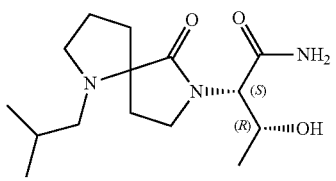 | RZ-450 |
| 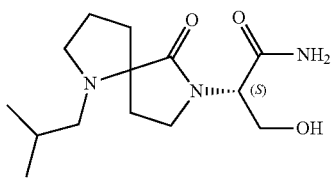 | RZ-451 |
| 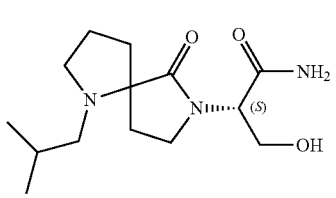 | RZ-452 |
| 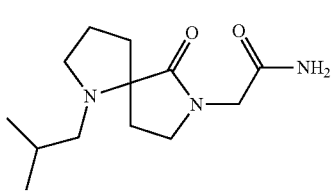 [SMILES: CC(C)CN1CCCC12CCN(CC(N)=O)C2=O] | RZ-453 |
| 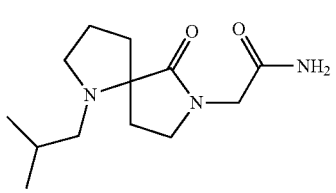 [SMILES: CC(C)CN1CCCC12CCN(CC(N)=O)C2=O] | RZ-454 |
| 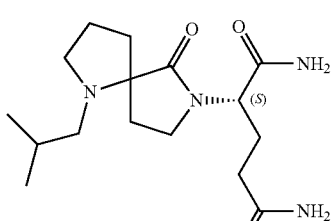 | RZ-455 |
| 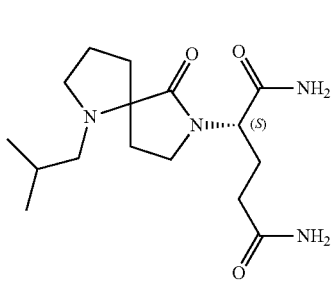 | RZ-456 |
| Structure | Compound |
|---|---|
| 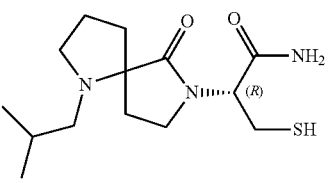 | RZ-457 |
| 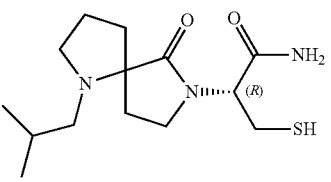 | RZ-458 |
| 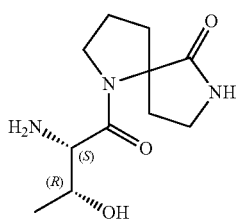 | RZ-459 |
| 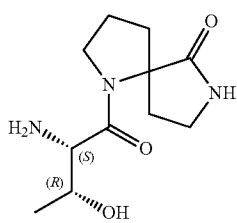 | RZ-460 |
| 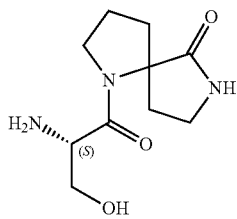 | RZ-461 |
| 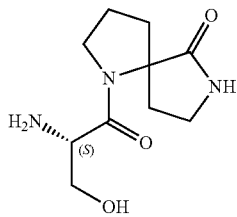 | RZ-462 |
|  | RZ-463 |

| Structure | Compound |
|---|---|
| 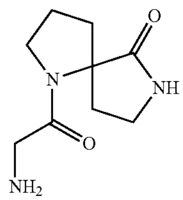 [SMILES: NCC(=O)N1CCCC12CCNC2=O] | RZ-464 |
| 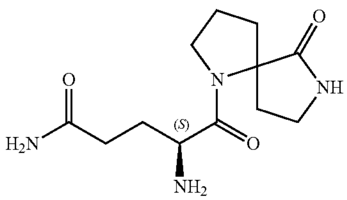 | RZ-465 |
| 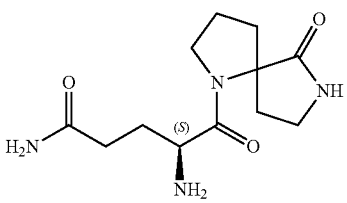 | RZ-466 |
| 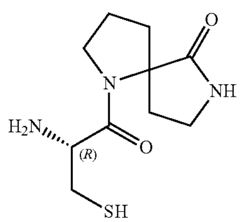 | RZ-467 |
| 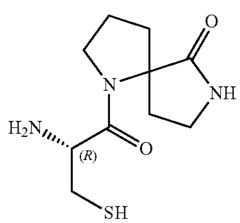 | RZ-468 |
| 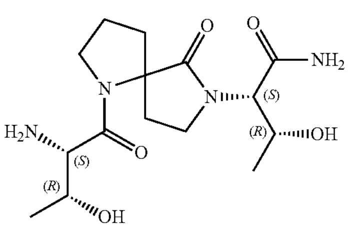 | RZ-469 |
| 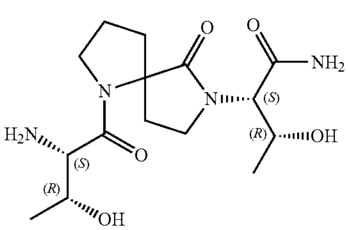 | RZ-470 |

| Structure | Compound |
|---|---|
| 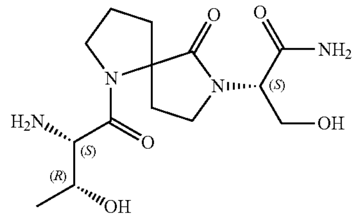 | RZ-471 |
| 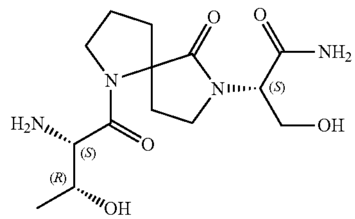 | RZ-472 |
| 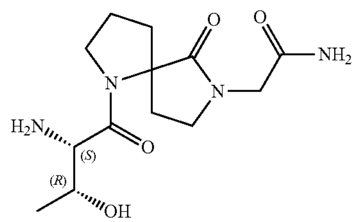 | RZ-473 |
| 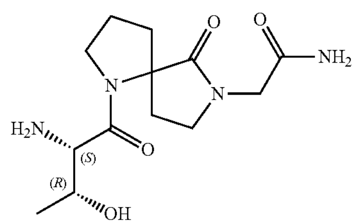 | RZ-474 |
| 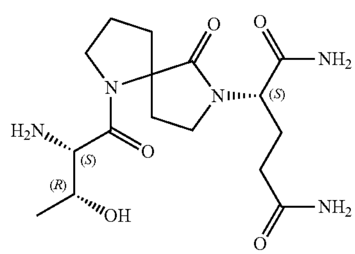 | RZ-475 |
| 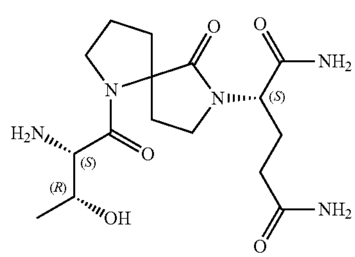 | RZ-476 |

| Structure | Compound |
|---|---|
| (structure) | RZ-477 |
| (structure) | RZ-478 |
| (structure) | RZ-479 |
| (structure) | RZ-480 |
| (structure) | RZ-481 |
| (structure) | RZ-482 |
| (structure) | RZ-483 |

| Structure | Compound |
|---|---|
| (structure) | RZ-484 |
| (structure) | RZ-485 |
| (structure) | RZ-486 |
| (structure) | RZ-487 |
| (structure) | RZ-488 |
| (structure) | RZ-489 |
| (structure) | RZ-490 |

| Structure | Compound |
|---|---|
| 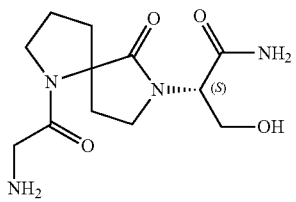 | RZ-491 |
| 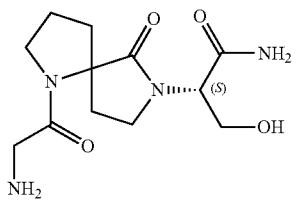 | RZ-492 |
| 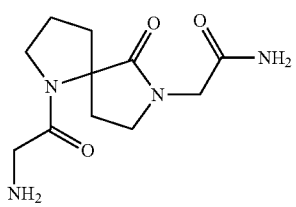 [SMILES: NCC(=O)N1CCCC12CCN(CC(N)=O)C2=O] | RZ-493 |
| 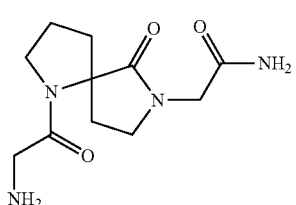 | RZ-494 |
| 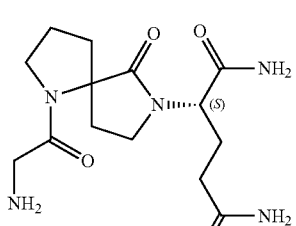 | RZ-495 |
| 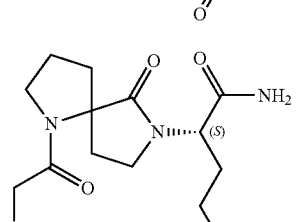 | RZ-496 |
| 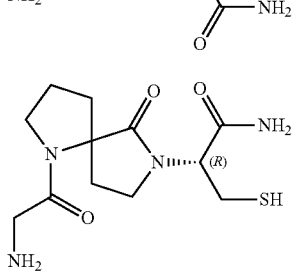 | RZ-497 |
| Structure | Compound |
|---|---|
| 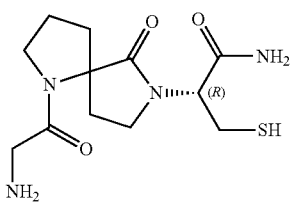 | RZ-498 |
| 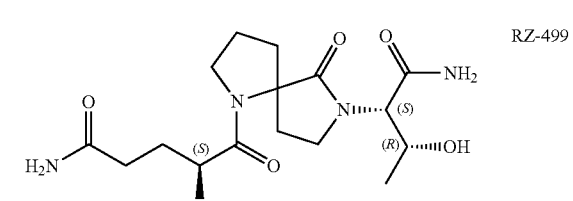 | RZ-499 |
| 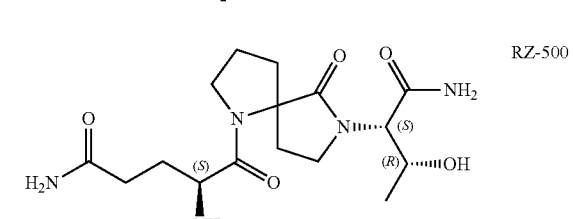 | RZ-500 |
| 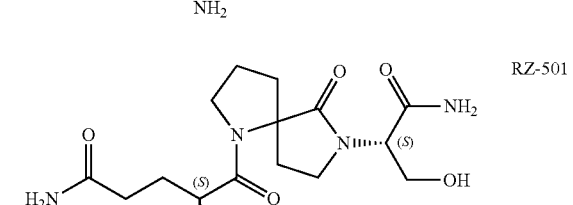 | RZ-501 |
| 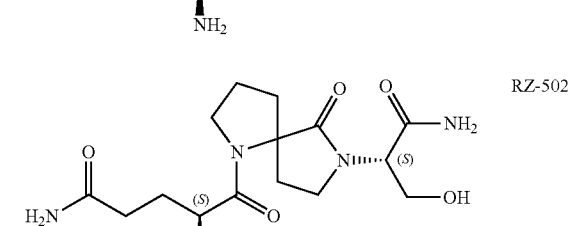 | RZ-502 |
| 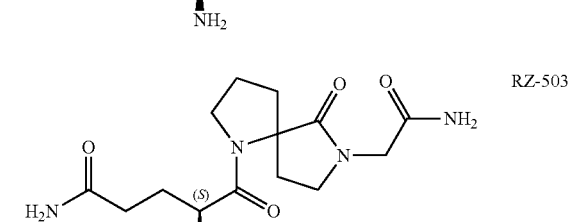 | RZ-503 |
| 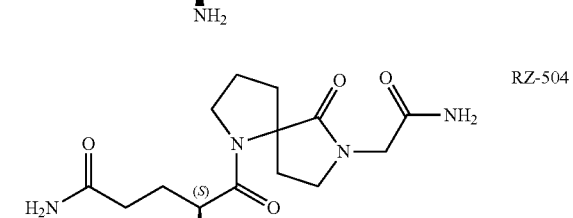 | RZ-504 |

| Structure | Compound |
|---|---|
| (structure) | RZ-505 |
| (structure) | RZ-506 |
| (structure) | RZ-507 |
| (structure) | RZ-508 |
| (structure) | RZ-509 |
| (structure) | RZ-510 |
| (structure) | RZ-511 |

| Structure | Compound |
|---|---|
| (structure) | RZ-512 |
| (structure) | RZ-513 |
| (structure) | RZ-514 |
| (structure) | RZ-515 |
| (structure) | RZ-516 |
| (structure) | RZ-517 |

| Structure | Compound |
|---|---|
| (structure diagram) | RZ-518 |

Example 5

This example demonstrates the positive emotional learning (PEL) test. Experiments were conducted as described in Burgdorf et al., "The effect of selective breeding for differential rates of 50-kHz ultrasonic vocalizations on emotional behavior in rats," Devel. Psychobiol., 51:34-46 (2009). Rat 50-kHz ultrasonic vocalization (hedonic USVs) is a validated model for the study of positive affective state and is best elicited by rough-and-tumble play. 50-kHz ultrasonic vocalizations have previously been shown to be positively correlated with reward and appetitive social behavior in rats, and to reflect a positive affective state.

The PEL assay measures the acquisition of positive (hedonic) 50-kHz ultrasonic vocalizations (USVs) to a social stimulus, heterospecific rough and tumble play stimulation. Heterospecific rough-and-tumble play stimulation was administered by the experimenter's right hand. One hour after administration of test compound or vehicle negative control (0.5% sodium carboxymethyl cellulose in 0.9% sterile saline vehicle), animals received 3 min of heterospecific rough-and-tumble play that consisted of alternating 15 sec blocks of heterospecific play and 15 sec of no-stimulation. High frequency ultrasonic vocalizations (USVs) were recorded and analyzed by sonogram with Avasoft SASlab Pro (Germany) as previously described by Burgdorf et al., "Positive emotional learning is regulated in the medial prefrontal cortex by GluN2B-containing NMDA receptors," Neuroscience, 192:515-523 (2011). Frequency modulated 50-kHz USVs that occurred during each of the no-stimulation periods were quantified to measure PEL. Animals were not habituated to play stimulation before testing. Positive emotional learning was measured during the conditioned stimulus (CS) trials preceding the tickle unconditioned stimulus (UCS) trials. Animals received 15 second trials consisting of 6 CS and 6 UCS trials each (3 min total).

The table below summarizes the findings. As each experiment includes its own vehicle group, an example (typical) vehicle score is shown. Max effect (mean number of 50 kHz USVs per 15 seconds) is reported as ^: <6.0; *: 6.0-7.6; : 7.7-10; *:10.1-20

| Compound | Route | Dose (mg/kg) | Max Effect |
|---|---|---|---|
| Vehicle | PO | NA | ^ |
| RE-1 | PO | .001-1 | *** |
| RA-1 | PO | 0.1 | *** |
| RB-1 | PO | .001-1 | *** |
| RC-1 | PO | .001-1 | *** |
| RW-1 | PO | 0.1 | ** |
| RM-1 | PO | .001-1 | *** |
| RT-1 | PO | 0.1 | ** |

Example 6

Assays were conducted as described by Moskal et al., "GLYX-13: a monoclonal antibody-derived peptide that acts as an N-methyl-D-aspartate receptor modulator," Neuropharmacology, 49, 1077-87, 2005. These studies were designed to determine if the test compounds act to facilitate NMDAR activation in NMDAR2A, NMDAR2B, NMDAR2C or NMDAR2D expressing HEK cell membranes as measured by increases in [$^3$H]MK-801 binding.

In the assay, 300 μg of NMDAR expressing HEK cell membrane extract protein was preincubated for 15 minutes at 25° C. in the presence of saturating concentrations of glutamate (50 μM) and varying concentrations of test compound ($1\times10^{-15}$M-$1\times10^{-7}$M), or 1 mM glycine. Following the addition of 0.3 μCi of [$^3$H]MK-801 (22.5 Ci/mmol), reactions were again incubated for 15 minutes at 25° C. (nonequilibrium conditions). Bound and free [$^3$H]MK-801 were separated via rapid filtration using a Brandel apparatus.

In analyzing the data, the DPM (disintegrations per minute) of [$^3$H]MK-801 remaining on the filter were measured for each concentration of test compound or for 1 mM glycine. The DPM values for each concentration of a ligand (N=2) were averaged. The baseline value was determined from the best fit curve of the DPM values modeled using the GraphPad program and the log(agonist) vs. response(three parameters) algorithm was then subtracted from all points in the dataset. The % maximal [$^3$H]MK-801 binding was then calculated relative to that of 1 mM glycine: all baseline subtracted DPM values were divided by the average value for 1 mM glycine. The $EC_{50}$ and % maximal activity were then obtained from the best fit curve of the % maximal [$^3$H]MK-801 binding data modelled using the GraphPad program and the log(agonist) vs. response(three parameters) algorithm.

The tables below summarize the results for the wild type NMDAR agonists NMDAR2A, NMDAR2B, NMDAR2C, and NMDAR2D, and whether the compound is not an agonist (−), is an agonist (+), or is a strong agonist (++), where column A is based on the % maximal [$^3$H]MK-801 binding relative to 1 mM glycine (−=0; <100%=+; and >100%=++); and column B is based on log $EC_{50}$ values (0=−; ≥$1\times10^{-9}$ M (e.g., −8)=+; and <$1\times10^{-9}$ M (e.g., −10)=++).

| Compound | NMDAR2A | | NMDAR2B | |
|---|---|---|---|---|
| | A | B | A | B |
| RE-1 | − | − | + | ++ |
| RA-1 | + | + | + | ++ |
| RB-1 | + | ++ | ++ | − |
| RC-1 | + | ++ | ++ | ++ |
| RW-1 | + | + | + | ++ |
| RX-1 | − | − | − | − |
| RM-1 | + | ++ | ++ | ++ |
| RT-1 | + | ++ | + | ++ |
| RG-619 | − | − | − | − |
| RG-603 | + | + | + | ++ |

| Compound | | | | |
|---|---|---|---|---|
| RG-601 | + | ++ | + | ++ |
| RG-602 | + | ++ | + | ++ |
| RG-605 | + | ++ | − | − |
| RG-606 | − | − | + | ++ |
| RG-623 | − | − | + | ++ |
| RG-621 | + | ++ | ++ | ++ |
| RG-609 | − | − | − | − |
| RG-610 | − | − | − | − |
| RZ-405 | + | ++ | ++ | + |
| RZ-406 | − | − | + | ++ |
| RZ-403 | − | − | ++ | ++ |
| RZ-404 | + | ++ | − | − |

| | NMDAR2C | | NMDAR2D | |
|---|---|---|---|---|
| Compound | A | B | A | B |
| RE-1 | − | − | + | ++ |
| RA-1 | + | ++ | − | − |
| RB-1 | + | ++ | + | + |
| RC-1 | + | ++ | + | ++ |
| RM-1 | + | ++ | + | ++ |
| RG-601 | + | ++ | ++ | ++ |
| RG-602 | ++ | + | + | ++ |
| RG-605 | − | − | − | − |
| RG-606 | − | − | − | − |
| RC-1 | − | − | − | − |
| RZ-405 | + | ++ | + | ++ |

Example 7

Sprague Dawley rats were dosed intravenously using a normal saline formulation containing 2 mg/kg of the compounds identified in the below table (except for the first four compounds that were delivered in 5 NMP, 5% Solutol® HS and 90% normal saline formulation). The table below summarizes the results of the IV pharmacokinetics.

| Compound | $C_0$ (ng/mL) | $AUC_{last}$ (hr*ng/mL) | $T_{1/2}$ (hr) | Cl (mL/min/kg) | $V_{ss}$ (L/kg) |
|---|---|---|---|---|---|
| RE-1 | 589.9 | 135.9 | 0.27 | NR | 4.12 |
| RA-1 | 1247.08 | 234.08 | 0.19 | NR | 1.69 |
| RB-1 | 2065.2 | 1261 | 3.35 | 25.81 | 2.79 |
| RC-1 | 2013.4 | 1511.4 | 1.36 | 21.81 | 1.84 |
| RG-603 | 5193 | 1568 | 0.99 | 21.1 | 0.81 |
| RG-601 | 2847 | 2279 | 1.16 | 13.53 | 1.14 |
| RG-605 | 3361 | 1576 | 0.3 | 20.99 | 0.53 |
| RG-606 | 2303 | 804 | 0.34 | 41.29 | 0.91 |
| RG-623 | 4134 | 10519 | 3.98 | 3.18 | 0.56 |
| RG-621 | 4759.45 | 6231.79 | 1.71 | 5.33 | 0.52 |
| RM-1 | 2009.24 | 1328.09 | 0.49 | 24.89 | 0.91 |
| RZ-405 | 3040.6 | 7007.7 | 4.05 | 4.74 | 0.69 |

In another experiment, Sprague Dawley rats were dosed per os using a normal saline formulation containing 10 mg/kg of the compounds identified in the table below (except for the first four compounds that were delivered in 5% NMP, 5% Solutol® HS and 90% normal saline formulation). Plasma, brain, and CSF samples were analyzed at various time points over a 24 hour period. The table below summarizes the results of the oral pharmacokinetics.

| Compound | $T_{max}$ (hr) | $C_{max}$ (ng/mL) | $AUC_{last}$ (hr * ng/mL) | CSF $C_{max}$ (ng/mL) | Brain $C_{max}$ (ng/mL) | % F |
|---|---|---|---|---|---|---|
| RE-1 | 0.25 | 495.17 | 272.7 | 86.1 | 22 | 40 |
| RA-1 | 0.25 | 592 | 324.2 | 102.5 | 203.6 | 28 |
| RB-1 | 1.17 | 825.1 | 3288 | 27.4 | 40.2 | 52 |
| RC-1 | 1.67 | 990.2 | 3668.7 | 20.8 | 27.6 | 49 |
| RG-603 | 1 | 311 | 897 | — | — | 11 |
| RG-601 | 0.83 | 3989 | 9509 | 1151 | 1447 | 83 |
| RG-605 | 0.25 | 6478 | 6370 | 1211 | 733 | 81 |
| RG-606 | 0.25 | 2812 | 1933 | 1077 | 612 | 48 |
| RG-623 | 0.42 | 10891 | 42553 | 4727 | 4317 | 81 |
| RG-621 | 0.58 | 12037.25 | 29103.5 | 3654.37 | 1977.29 | 93 |
| RW-1 | 1 | 4074 | NR | 853 | NR | NR |
| RM-1 | 0.25 | 4309.99 | 5008.61 | 1415 | 2763 | 75 |
| RZ-405 | 0.5 | 10783 | 29521 | 3157 | 2209 | 84 |

Example 8

A non-clinical in vivo pharmacology study (Porsolt assay) was performed to measure antidepressant-like effects. A negative control (0.5% sodium carboxymethyl cellulose in 0.9% sterile saline vehicle) and a positive control (fluoxetine) are shown for comparison against test compound. The study allowed for the evaluation of the effects of each compound on the Porsolt forced swim test as assessed by the rats' response (reduced floating time) during a 5-minute swimming test.

Male 2-3 month old Sprague Dawley rats were used (Harlan, Indianapolis, Ind.). Rats were housed in Lucite cages with aspen wood chip bedding, maintained on a 12:12 light:dark cycle (lights on at 5 AM), and given ad libitum access to Purina lab chow (USA) and tap water throughout the study.

The Porsolt forced swim test adapted for use in rats was performed as described by Burgdorf et al., (The long-lasting antidepressant effects of rapastinel (GLYX-13) are associated with a metaplasticity process in the medial prefrontal cortex and hippocampus. Neuroscience 308:202-211, 2015). Animals were placed in a 46 cm tall×20 cm in diameter clear glass tube filled to 30 cm with tap water (23±1° C.) for 15 min on the first day (habituation) and 5 min on the subsequent test day. Positive control fluoxetine was dosed 3 times (24 h, 5 h and 1 h) prior to testing. Animals were tested 1 h or 24 h post-dosing with the test compounds or vehicle. Animals received a 15 min habituation session 1 day before the 5 min test. A subset of compounds tested at 1 h post-dosing were retested at 1 wk post-dosing in the same sets of animals. Water was changed after every other animal. Animals were videotaped, and floating time as defined as the minimal amount of effort required to keep the animals head above water was scored offline by a blinded experimenter with high inter-rater reliability (Pearson's r>0.9).

The results for test compounds are shown in the table below. Each compound tested at dose level shown. Significance vs. vehicle group for each experiment is marked. A compound marked "Yes" was found to be statistically significant (p<=0.05) from vehicle at dose level shown. A compound marked "No" was not statistically significant from vehicle. Data was averaged for test compound and vehicle groups (N approximately 8 per group) and the percent reduction in floating for group treated with test compound relative to group treated with vehicle is shown.

| Compound | 1 h post-dose ||| 24 h post-dose ||| 1 wk post-dose |||
|---|---|---|---|---|---|---|---|---|---|
| | Dose (mg/kg) | Significance vs. vehicle | % reduction in float time | Dose (0.1 mg/kg) | Significance vs. vehicle | % reduction in float time | Dose (0.1 mg/kg) | Significance vs. vehicle | % reduction in float time |
| Fluoxetine | 20 | Yes | 54% | NA | NA | NA | NA | NA | NA |
| RG-601 | 0.1 | Yes | 82.7% | NR | NR | NR | 0.1 | Yes | 34.4% |
| RG-602 | 0.1 | Yes | 71.1% | NR | NR | NR | 0.1 | Yes | 55.5% |
| RG-623 | 0.1 | Yes | 60.0% | 0.1 | Yes | 52.9% | NR | NR | NR |
| RZ-405 | 0.1 | Yes | 78.9% | 0.1 | Yes | 42.7% | NR | NR | NR |

EQUIVALENTS

Those skilled in the art will recognize, or be able to ascertain using no more than routine experimentation, many equivalents to the specific embodiments of the disclosure described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

What is claimed is:

1. A compound represented by:

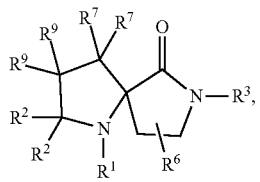

or a pharmaceutically acceptable salt and/or a stereoisomer thereof, wherein:

$R^1$ is selected from the group consisting of $C_1$-$C_6$alkyl, phenyl,

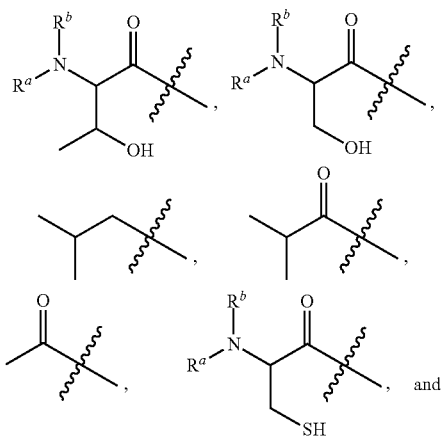

wherein $C_1$-$C_6$ alkyl substituted by one, two or three substituents each independently selected from —C(O)NR$^a$R$^b$, —NR$^a$R$^b$, hydroxyl, S(O)$_w$—$C_1$-$C_3$alkyl, SH, phenyl and halogen, and wherein phenyl is substituted by one, two or three substituents independently selected for each occurrence from —C(O)—$C_1$-$C_3$alkyl, hydroxyl, —C(O)—$C_1$-$C_3$alkyl, methyl, $CF_3$ and halogen;

$R^7$ is independently selected from the group consisting of H, —$C_1$-$C_6$alkyl, —S(O)$_w$—$C_1$-$C_3$alkyl, and halogen;

$R^9$ is independently selected from the group consisting of H, —$C_1$-$C_6$alkyl, —S(O)$_w$—$C_1$-$C_3$alkyl, and halogen, or one $R^7$ and one $R^9$ taken together with the adjacent carbons to which they are attached form a 3-membered carbocyclic ring which can be optionally substituted by one or two substituents independently selected from the group consisting of halogen, hydroxyl, —$C_1$-$C_3$alkyl, —$C_1$-$C_3$alkoxy, —C(O)NR$^a$R$^b$, and —NR$^a$R$^b$;

$R^2$ is independently selected for each occurrence from the group consisting of H, $C_1$-$C_6$alkyl, —S(O)$_w$—$C_1$-$C_3$alkyl, —NR$^a$R$^b$ and halogen;

$R^6$ represents one or two optional substitutions each on one or more available ring carbons, and is independently selected for each occurrence from the group consisting of $C_1$-$C_6$alkyl, —S(O)$_w$—$C_1$-$C_3$alkyl, —NR$^a$R$^b$ and halogen;

$w$ is 0, 1, or 2;

$R^3$ is selected from the group consisting of H, $C_1$-$C_6$ alkyl, —C(O)R$^{31}$ and —C(O)OR$^{32}$;

$R^{31}$ and $R^{32}$ are each independently selected from the group consisting of H, $C_1$-$C_6$alkyl, —$C_3$-$C_6$cycloalkyl, and phenyl; and $R^a$ and $R^b$ are each independently for each occurrence selected from the group consisting of H, phenyl, and $C_1$-$C_3$alkyl, or $R^a$ and $R^b$ taken together with the nitrogen to which they are attached form a 4-6 membered heterocyclic ring;

wherein any aforementioned $C_1$-$C_6$ alkyl of $R^2$, $R^3$, $R^5$, $R^6$, $R^7$, $R^9$, $R^{31}$ and $R^{32}$, independently for each occurrence, is optionally substituted by one, two or three substituents each independently selected from —C(O)NR$^a$R$^b$, —NR$^a$R$^b$, hydroxyl, S(O)$_w$—C$_1$-C$_3$alkyl, SH, phenyl and halogen, and any aforementioned phenyl, independently for each occurrence, is optionally substituted by one, two or three substituents each independently selected from —C(O)—C$_1$-C$_3$alkyl, hydroxyl, methyl, CF$_3$ and halogen.

2. The compound of claim 1, wherein R$^1$ is

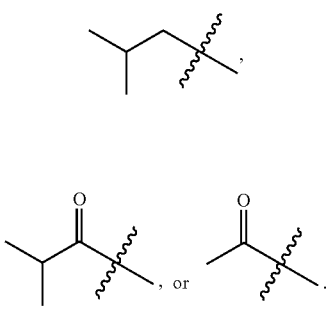

3. The compound of claim 1, wherein R$^3$ is H.
4. The compound of claim 1, wherein R$^3$ is selected from the group consisting of:

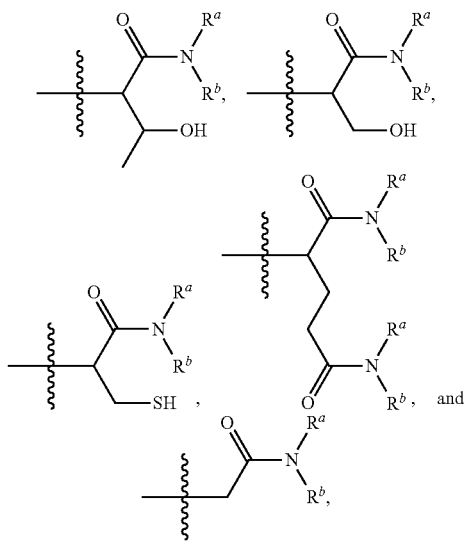

wherein R$^a$ and R$^b$ are each independently selected for each occurrence from the group consisting of hydrogen and —C$_1$-C$_3$.

5. The compound of claim 1, wherein R$^2$ is H at each occurrence.
6. The compound of claim 1, wherein R$^7$ is H at each occurrence.
7. The compound of claim 1, wherein the compound is:

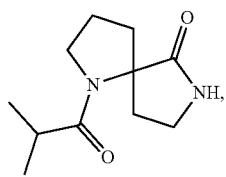

or a pharmaceutically acceptable salt and/or a stereoisomer thereof.

8. The compound of claim 1, selected from the group consisting of:

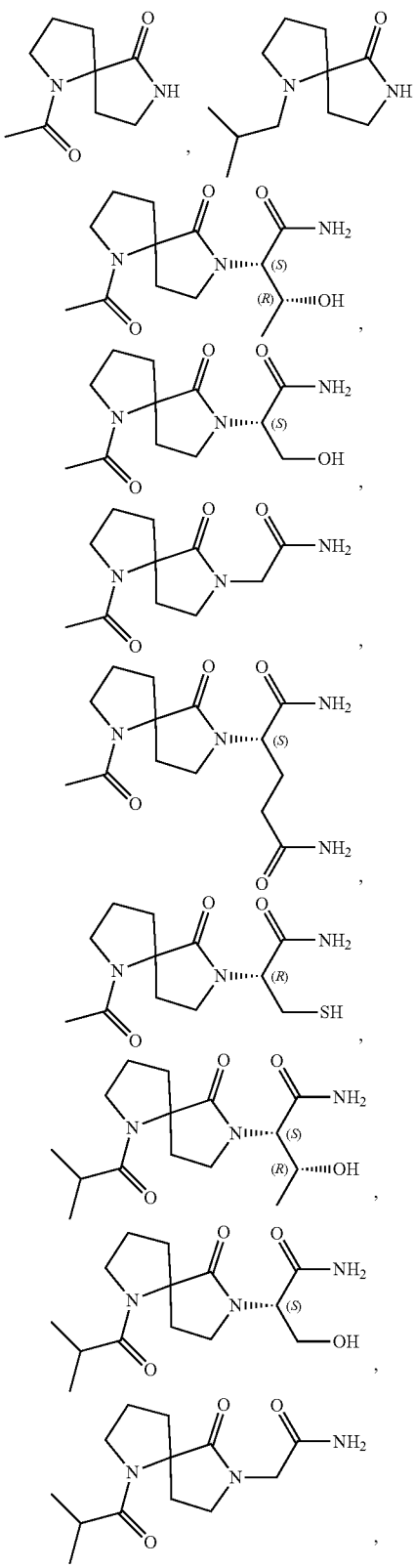

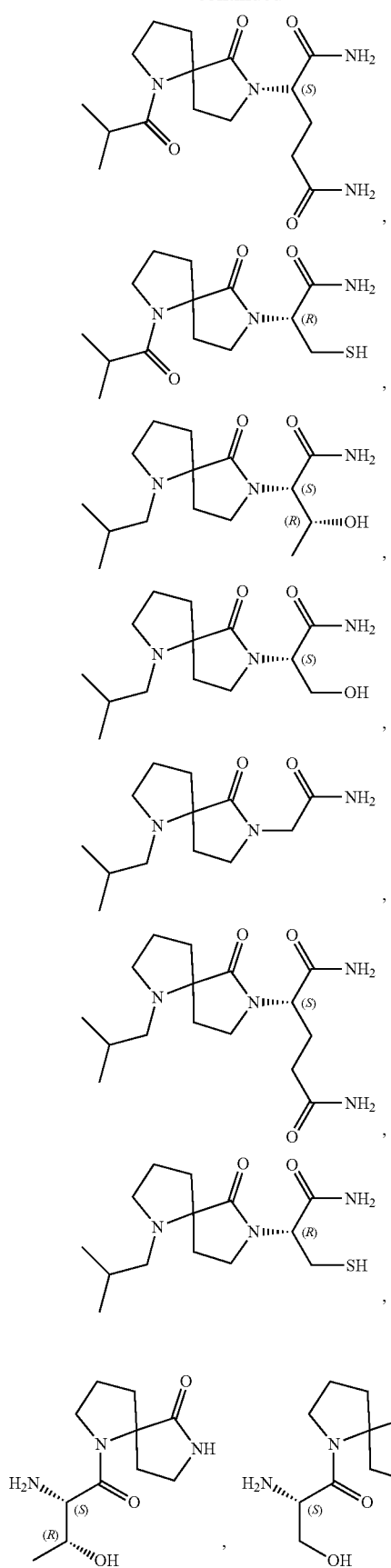
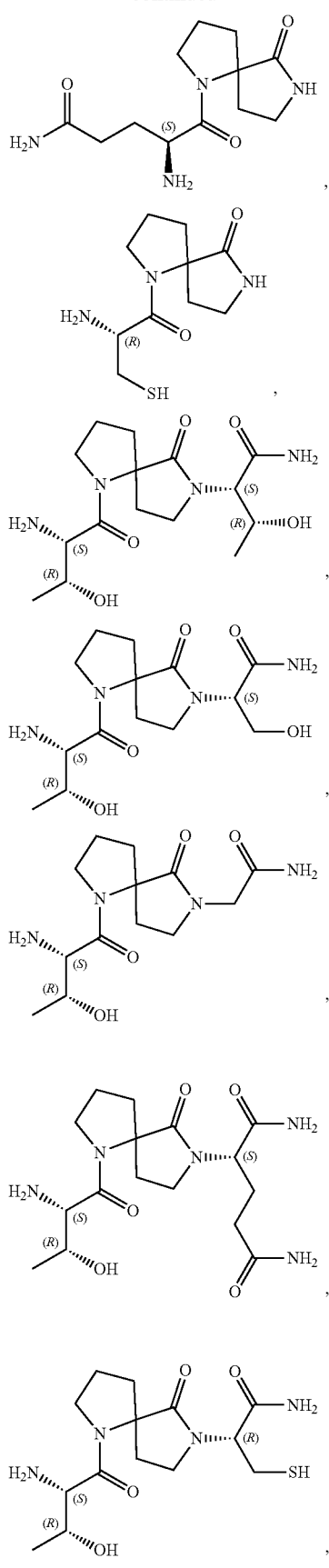

-continued
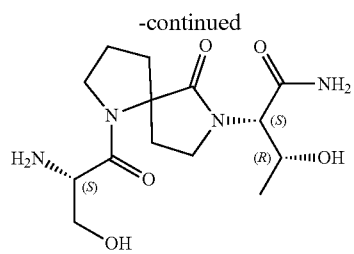
,
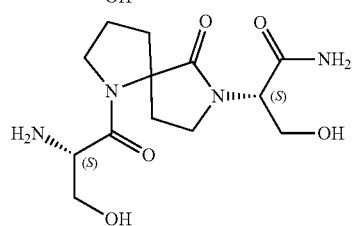
,
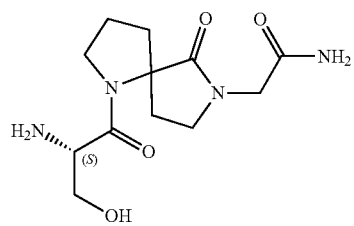
,
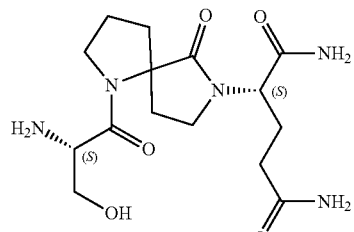
,
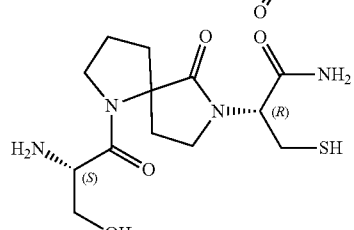
,
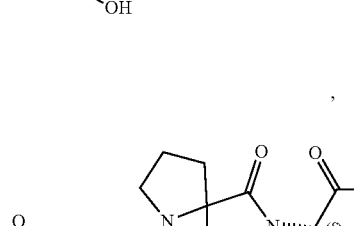
,
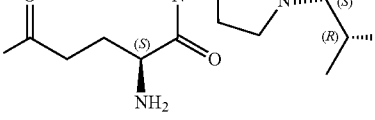
,
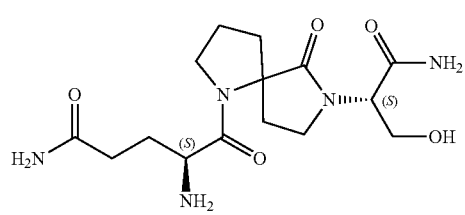
,
-continued
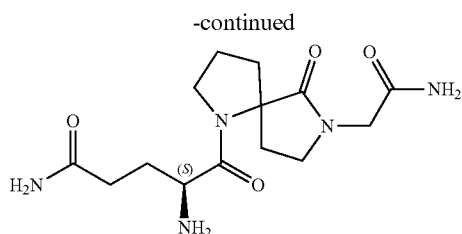
,
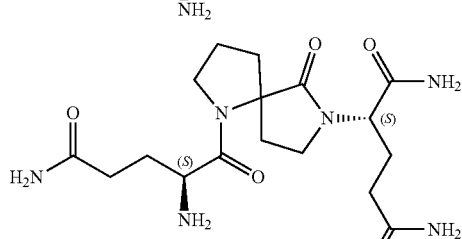
,
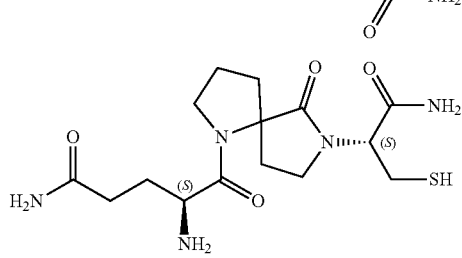
,
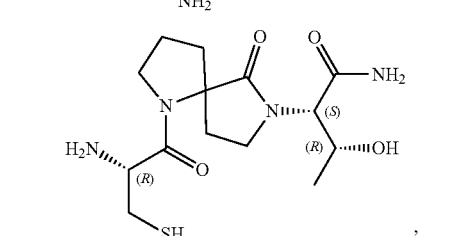
,
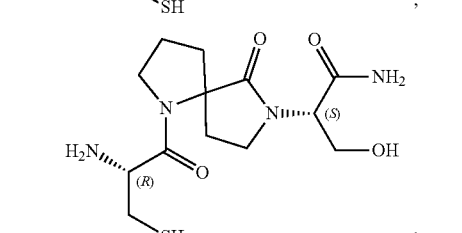
,
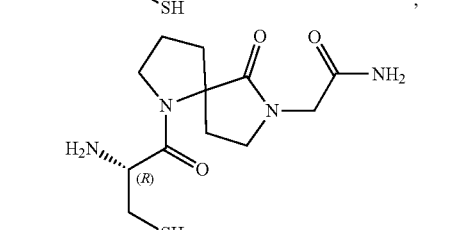
,
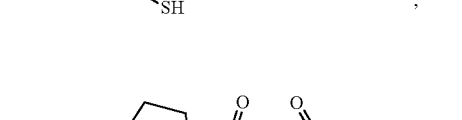
,
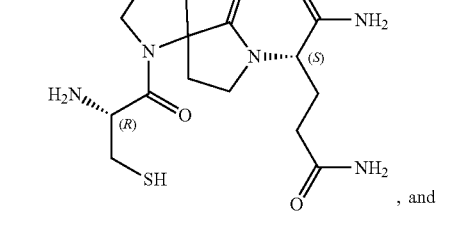
, and -continued

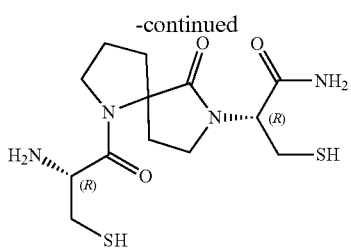

, or a pharmaceutically acceptable salt and/or a stereoisomer thereof.

9. The compound of claim 1, wherein $R^1$ is —C(O)—$C_1$-$C_6$alkyl.

10. The compound of claim 1, wherein $R^1$ is

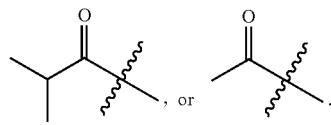

, or .

11. The compound of claim 1, wherein $R^1$ is

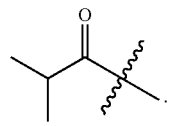

.

12. The compound of claim 1, wherein $R^9$ is H at each occurrence.

13. The compound of claim 1, wherein $R^6$ is absent.

14. The compound of claim 1, wherein each $R^2$, $R^7$ and $R^9$ is H.

15. The compound of claim 14, wherein $R^6$ is absent.

16. A pharmaceutical composition comprising a compound of claim 1, and a pharmaceutically acceptable excipient.

17. A pharmaceutical composition comprising a compound of claim 7, and a pharmaceutically acceptable excipient.

18. A pharmaceutical composition comprising a compound of claim 8, and a pharmaceutically acceptable excipient.

* * * * *